United States Patent
Ide

(10) Patent No.: US 11,172,814 B2
(45) Date of Patent: Nov. 16, 2021

(54) ANTIFOGGING DEVICE, ENDOSCOPE DEVICE AND METHOD OF MANUFACTURING ANTIFOGGING DEVICE

(71) Applicant: OLYMPUS CORPORATION, Tokyo (JP)

(72) Inventor: Takayuki Ide, Akishima (JP)

(73) Assignee: OLYMPUS CORPORATION, Tokyo (JP)

( * ) Notice: Subject to any disclaimer, the term of this patent is extended or adjusted under 35 U.S.C. 154(b) by 754 days.

(21) Appl. No.: 15/912,635

(22) Filed: Mar. 6, 2018

(65) Prior Publication Data
US 2018/0192862 A1 Jul. 12, 2018

Related U.S. Application Data

(63) Continuation of application No. PCT/JP2015/076791, filed on Sep. 18, 2015.

(51) Int. Cl.
| | | |
|---|---|---|
| *A61B 1/12* | (2006.01) | |
| *A61B 1/00* | (2006.01) | |
| *G02B 23/24* | (2006.01) | |
| *G02B 27/00* | (2006.01) | |
| *G02B 7/02* | (2021.01) | |

(52) U.S. Cl.
CPC ............ *A61B 1/127* (2013.01); *A61B 1/0011* (2013.01); *A61B 1/128* (2013.01); *G02B 23/24* (2013.01); *G02B 27/0006* (2013.01); *G02B 7/028* (2013.01); *G02B 23/2476* (2013.01)

(58) Field of Classification Search
CPC .............................. A61B 1/127; G02B 27/0006
See application file for complete search history.

(56) References Cited

U.S. PATENT DOCUMENTS

| | | | |
|---|---|---|---|
| 2014/0221743 A1 | 8/2014 | Sugiyama | |
| 2015/0080657 A1 | 3/2015 | Ide | |
| 2015/0313454 A1* | 11/2015 | Ide ...................... | A61B 1/0008 |
| | | | 600/129 |

FOREIGN PATENT DOCUMENTS

| | | | | |
|---|---|---|---|---|
| JP | 2003-334157 A | 11/2003 | | |
| JP | 2006-090704 A | 4/2006 | | |
| JP | 2013-081656 A | 5/2013 | | |
| JP | 2014-155583 A | 8/2014 | | |
| JP | 2014155583 A | * 8/2014 | ......... | G02B 23/2469 |
| JP | 2015-058149 A | 3/2015 | | |

OTHER PUBLICATIONS

International Search Report dated Dec. 15, 2015 issued in PCT/JP2015/076791.

* cited by examiner

*Primary Examiner* — Alexandra L Newton
*Assistant Examiner* — Rynae Boler
(74) *Attorney, Agent, or Firm* — Scully, Scott, Murphy & Presser, P.C.

(57) ABSTRACT

An antifogging device includes: a heater configured to apply heat to an optical member; a temperature sensor configured to detect a temperature; a circuit board with a surface mounted the heater and the temperature sensor; a sealing member that is made of a resin material and that is applied to the surface to seal the heater and the temperature sensor; and a joining part that is provided on at least part of the surface and that is made of an inorganic material, the joining part being configured to: extend along a periphery of the surface in a state of being exposed to a side surface of the circuit board; and contact the sealing member.

6 Claims, 17 Drawing Sheets

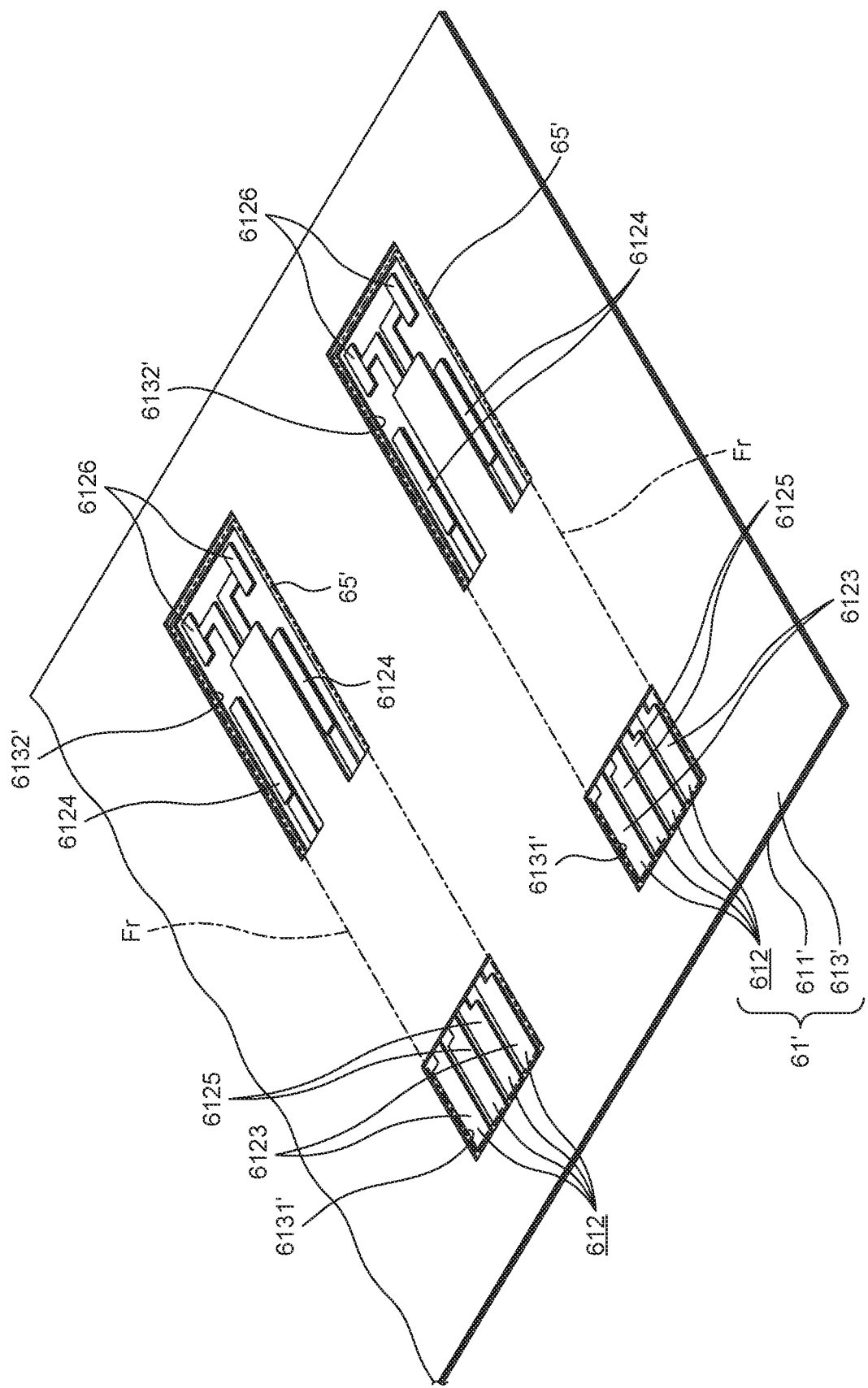

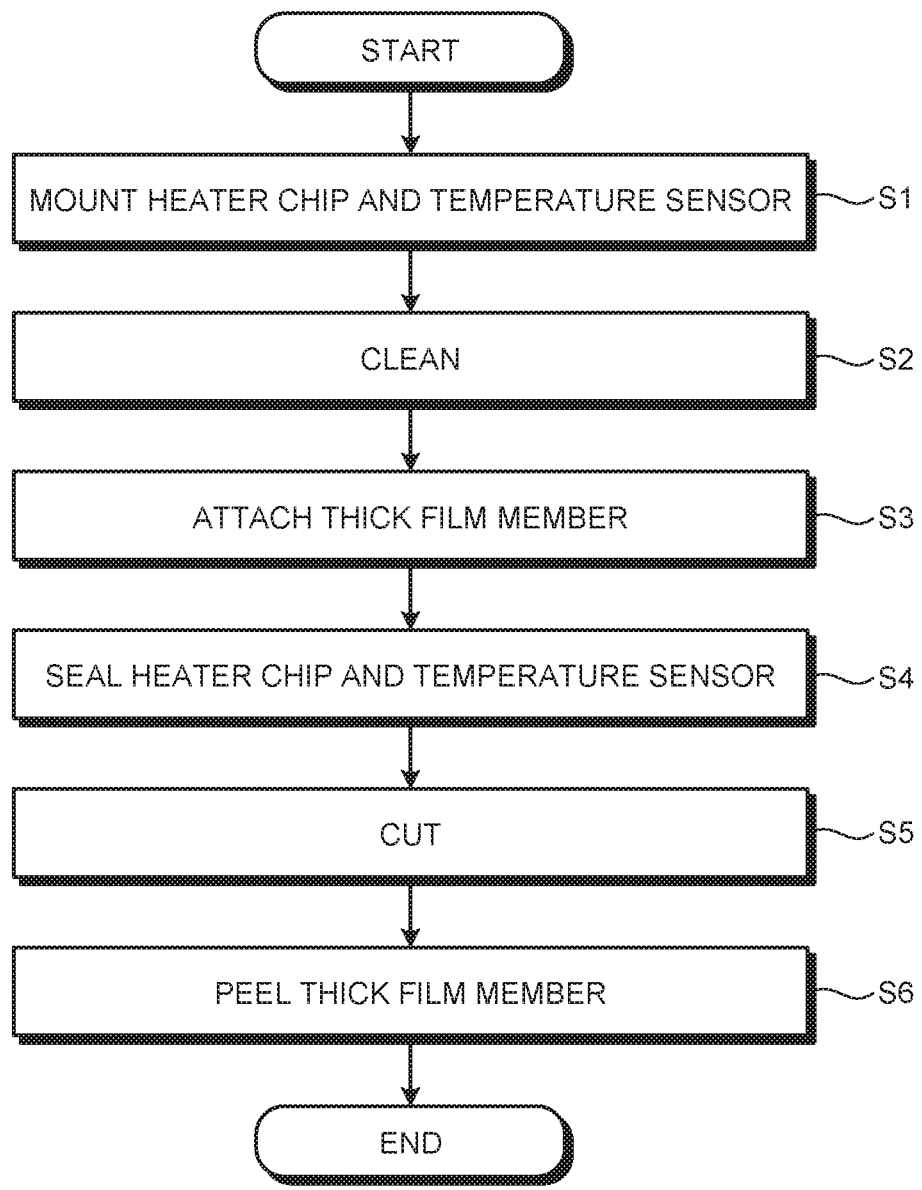

ANTIFOGGING DEVICE, ENDOSCOPE DEVICE AND METHOD OF MANUFACTURING ANTIFOGGING DEVICE

CROSS-REFERENCE TO RELATED APPLICATION

This application is a continuation-in-part of International Application No. PCT/JP2015/076791, filed on Sep. 18, 2015, the entire contents of which are incorporated herein by reference.

BACKGROUND

1. Technical Field

The disclosure relates to an antifogging device, an endoscope device including the antifogging device, and a method of manufacturing an antifogging device.

2. Related Art

In the related art, antifogging devices each preventing fogging occurring on an optical member, such as a lens, have been proposed (see, for example, Japanese Laid-open Patent Publication No. 2003-334157).

According to the invention described in Japanese Laid-open Patent Publication No. 2003-334157, the above-described antifogging device is mounted on an endoscope device that inserts its insertion unit into a subject and captures in-vivo images of the subject while applying illumination light from the distal end of the insertion unit to perform in-vivo observation on the subject.

Specifically, in the antifogging device described in Japanese Laid-open Patent Publication No. 2003-334157, a temperature sensor is provided to the distal end of the insertion unit and, based on the result of detection by the temperature sensor, heating light is applied to an optical member, such as an objective lens, that is provided to the distal end of the insertion unit to prevent fogging occurring on the optical member.

Furthermore, in the related art, a temperature sensor including an insulative substrate on which a land made of a conductive foil is formed as a pattern and a heat sensitive element that is mounted on the insulative substrate and that electrically connects to the land has been proposed (see, for example, Japanese Laid-open Patent Publication No. 2006-90704).

Specifically, in the temperature sensor described in Japanese Laid-open Patent Publication No. 2006-90704, after a sensor substrate is inserted into a pipe, the pipe (the surrounding of the sensor substrate) is filled with an insulative resin and the insulative resin is cured in order to perform insulative sealing on the heat sensitive element.

SUMMARY

In some embodiments, an antifogging device includes: a heater configured to apply heat to an optical member; a temperature sensor configured to detect a temperature; a circuit board with a surface mounted the heater and the temperature sensor; a sealing member that is made of a resin material and that is applied to the surface to seal the heater and the temperature sensor; and a joining part that is provided on at least part of the surface and that is made of an inorganic material, the joining part being configured to: extend along a periphery of the surface in a state of being exposed to a side surface of the circuit board; and contact the sealing member.

In some embodiments, an endoscope device includes: an optical member; and the antifogging device configured to prevent fogging occurring on the optical member.

In some embodiments, a method of manufacturing an antifogging device in which a heater and a temperature sensor are arranged on a circuit board that includes, before the manufacturing, a first area where the heater and the temperature sensor are arranged and a third area that is provided outside the first area and that has a joining part made of an inorganic material in at least part of a boundary between the first area and the third area on the circuit board, the method includes: arranging the heater and the temperature sensor on the circuit board; sealing the heater and the temperature sensor by applying, over the first area and the third area, a sealing member made of a resin material on a surface of the circuit board on which the heater and the temperature sensor are arranged; and cutting the circuit board along the boundary between the first area and the third area.

In some embodiments, a method of manufacturing an antifogging device in which a heater and a temperature sensor are arranged on a circuit board that includes, before the manufacturing, a first area where the heater and the temperature sensor are arranged and a third area that is provided outside the first area, the method includes: arranging the heater and the temperature sensor on the circuit board; sealing the heater and the temperature sensor by applying, over the first area and the third area, a sealing member made of a resin material on a surface of the circuit board on which the heater and the temperature sensor are arranged; and cutting the circuit board along a boundary between the first area and the third area.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 8 is a perspective view illustrating a flexible substrate that is prepared before a method of manufacturing the antifogging device illustrated in FIGS. 3 to 5 is performed;

FIG. 9 is a flowchart illustrating the method of manufacturing the antifogging device illustrated in FIGS. 3 to 5;

FIG. 100 is a diagram illustrating the method of manufacturing the antifogging device illustrated in FIG. 9;

DETAILED DESCRIPTION

Figure 1:
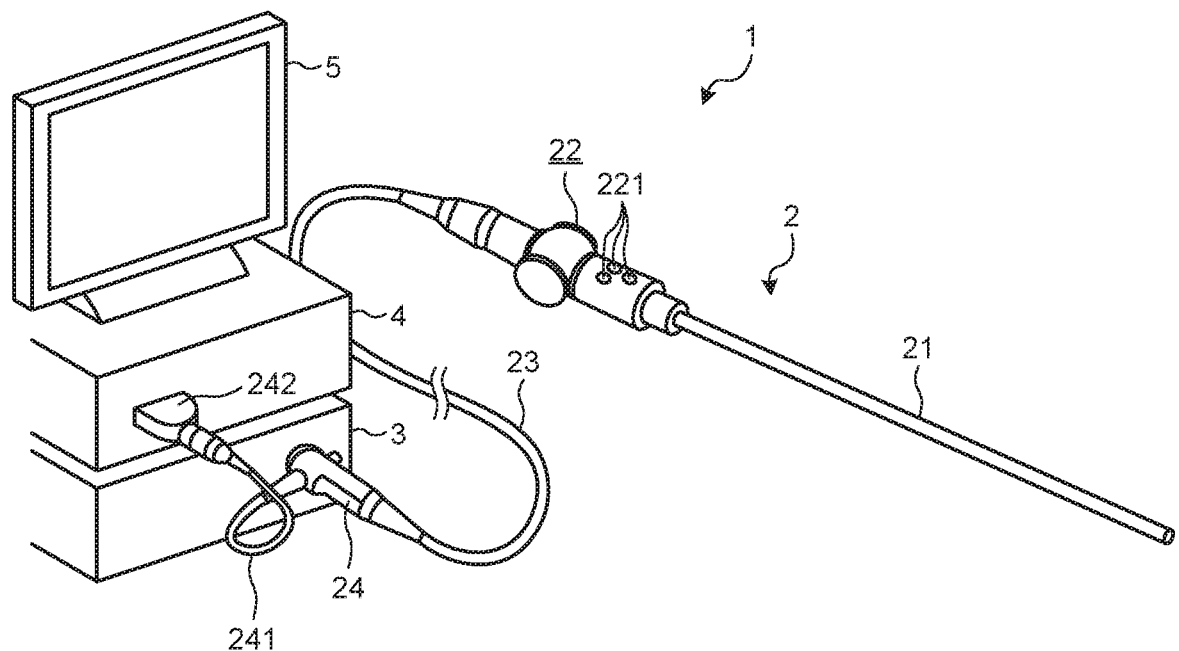
FIG. 1 is a diagram illustrating a schematic configuration of an endoscope device according to a first embodiment of the disclosure.

Modes for carrying out the disclosure (hereinafter, referred to as "embodiments") will be described below with reference to the accompanying drawings. The embodiments do not limit the disclosure. Furthermore, in the illustrations in the drawings, the same components are denoted with the same reference numbers.

First Embodiment

Schematic Configuration of Endoscope Device

FIG. 1 is a diagram illustrating a schematic configuration of an endoscope device 1 according to a first embodiment of the disclosure.

The endoscope device 1 is a device that is used in the field of medicine and that performs in-vivo observation on a subject (a living body). As illustrated in FIG. 1, the endoscope device 1 includes an endoscope 2, a light source device 3, a control device 4 and a display device 5.

The endoscope 2 is partly insertable into a living body, captures in-vivo images, and outputs imaging signals.

The detailed configuration of the endoscope 2 will be described below.

An endoscope connector 24 of the endoscope 2, which will be described below, is detachably connected to the light source device 3 and the light source device 3 supplies illumination light that illuminates the inside of the living body to the endoscope 2 via the endoscope connector 24.

An electronic connector 242 that is provided at the distal end of an electronic cable 241 extending from the endoscope connector 24 is detachably connected to the control device 4. The control device 4 outputs control signals to the endoscope 2 and imaging signals from the endoscope 2 are input to the control device 4 via the endoscope connector 24 (the electronic connector 242 and the electronic cable 241). The control device 4 generates endoscopic images by performing given processing on the imaging signals.

The display device 5 is made of liquid crystals or electro luminescence. The display device 5 displays the endoscopic images that are generated by the control device 4, etc.

Configuration of Endoscope

As illustrated in FIG. 1, the endoscope 2 includes an insertion unit 21, an operating unit 22, a universal cable 23 and the endoscope connector 24.

In the endoscope 2 (the insertion unit 21, the operating unit 22, the universal cable 23 and the endoscope connector 24), two light guides LG (see FIG. 2) that transmit the illumination light supplied from the light source device 3 (see FIG. 2), an imaging cable (not illustrated) for endoscopic observation (for transmitting control signals and imaging signals), a control cable (not illustrated) for controlling an antifogging device 6 (see FIG. 2), which will be described below, etc., are provided.

Figure 2:
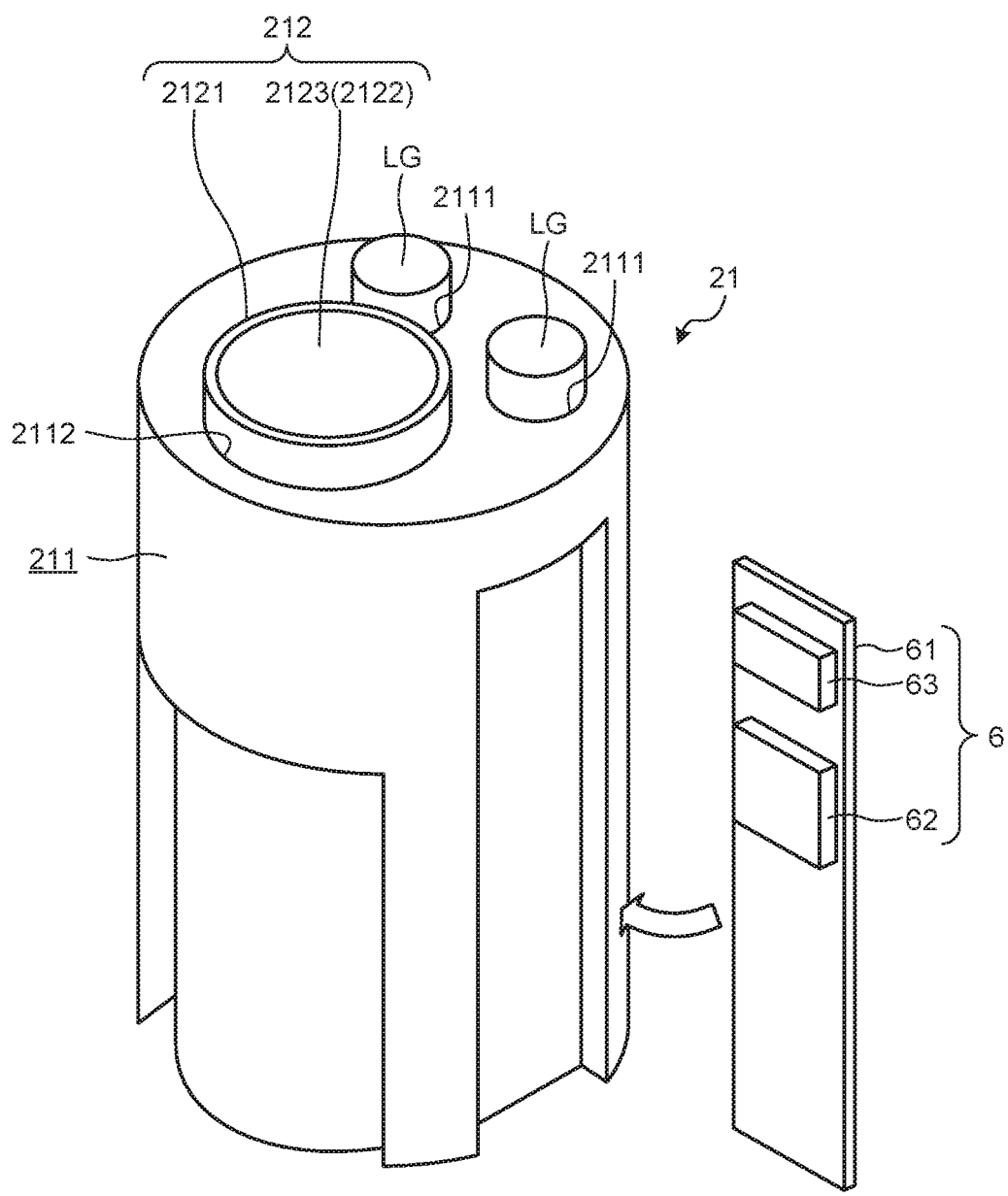
FIG. 2 is a diagram schematically illustrating a distal end part of the insertion unit illustrated in FIG. 1.

FIG. 2 is a diagram schematically illustrating the distal end part of the insertion unit 21.

The insertion unit 21 is rigid and elongated. The insertion unit 21 is inserted into the living body. As illustrated in FIG. 2, a frame member 211 is provided at the distal end of the insertion unit 21.

The frame member 211 has a shape of a cylinder with a bottom. The frame member 211 is attached to the insertion unit 21 such that the bottom is positioned at the distal end of the insertion unit 21. As illustrated in FIG. 2, two illumination windows 2111 that connect the inside and the outside and an observation window 2112 are formed on the bottom.

The two illumination windows 2111 are holes for applying the illumination light to the inside of the living body. As illustrated in FIG. 2, the output ends of the above-described two light guides LG are inserted into the two illumination windows 2111, respectively.

The observation window 2112 is a hole for acquiring optical in-vivo images. As illustrated in FIG. 2, an imaging unit 212 is attached to the inside of the observation window 2112.

As illustrated in FIG. 2, the imaging unit 212 includes a cylindrical lens frame 2121, an imaging optical system 2122, and an imaging device (not illustrated).

The imaging optical system 2122 is provided in the lens frame 2121. The imaging optical system 2122 includes at least one lens. The imaging optical system 2122 focuses light of an optical in-vivo image via the observation window 2112.

In the first embodiment, in the imaging optical system 2122, an objective lens 2123 (FIG. 2) is used as a member (the optical member according to the disclosure) having a surface exposed to the outside of the insertion unit 21. Alternatively, a cover glass, or the like, may be used.

The imaging device is provided inside the lens frame 2121. The imaging device captures an optical image of light focused by the imaging optical system 2122 and outputs imaging signals obtained by the image capturing. The imaging signals that are output from the imaging device are transmitted to the control device 4 via the above-described imaging cable.

The endoscope 2 is normally set in an environment where the temperature and the humidity are controlled, such as a treatment room. The distal end part of the insertion unit 21 is therefore exposed to the controlled temperature and humidity before the endoscope 2 is used. When the insertion unit 21 is inserted into a living body, fogging occurs on the objective lens 2123 due to, for example, the difference between the room temperature and the body temperature, the in-vivo environment where the humidity is high (at about 98 to 100%), which significantly lowers the imaging field of view.

To deal with fogging, as illustrated in FIG. 2, the antifogging device 6 that prevents fogging occurring on the objective lens 2123 is attached to a side surface of the frame member 211.

The detailed configuration of the antifogging device 6 will be described below.

The operating unit 22 is a unit that is connected to the proximal end side of the insertion unit 21 and that receives various types of operations from a doctor, or the like. As illustrated in FIG. 1, the operating unit 22 is provided with switches 221 for performing various types of operations.

As illustrated in FIG. 1, the universal cable 23 is a cable having one end connected to the operating unit 22 and in which the above-described light guides LG, the imaging cables, the control cable, etc., are provided.

As illustrated in FIG. 1, the endoscope connector 24 is a connector that is provided at the other end of the universal cable 23 and is for connection to the light source device 3 and the control device 4.

In the first embodiment, as illustrated in FIG. 1, the electronic cable 241 having a distal end provided with the electronic connector 242 is extended to the endoscope connector 24. The endoscope connector 24 detachably connects directly to the light source device 3 and detachably connects to the control device 4 via the electronic cable 241 and the electronic connector 242.

Configuration of Antifogging Device

Figure 3:
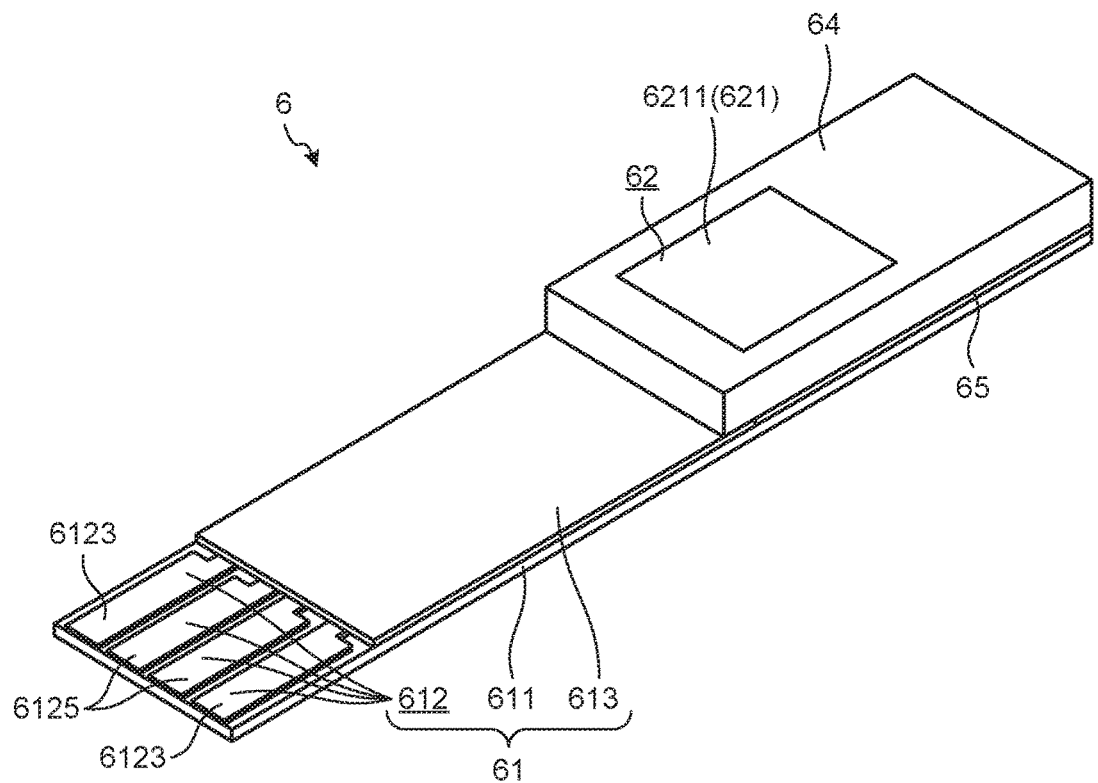
FIG. 3 is a perspective view illustrating the antifogging device illustrated in FIG. 2.
Figure 4:
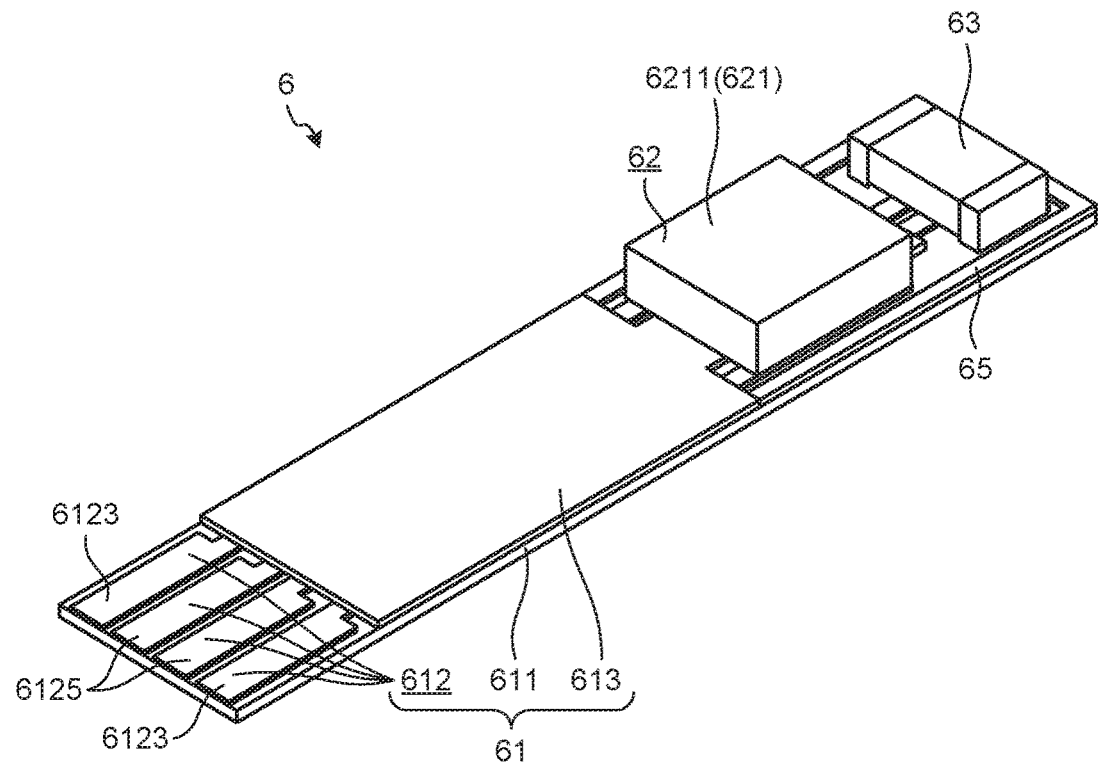
FIG. 4 is a diagram obtained by omitting the sealing member from what illustrated in FIG. 3.
Figure 5:
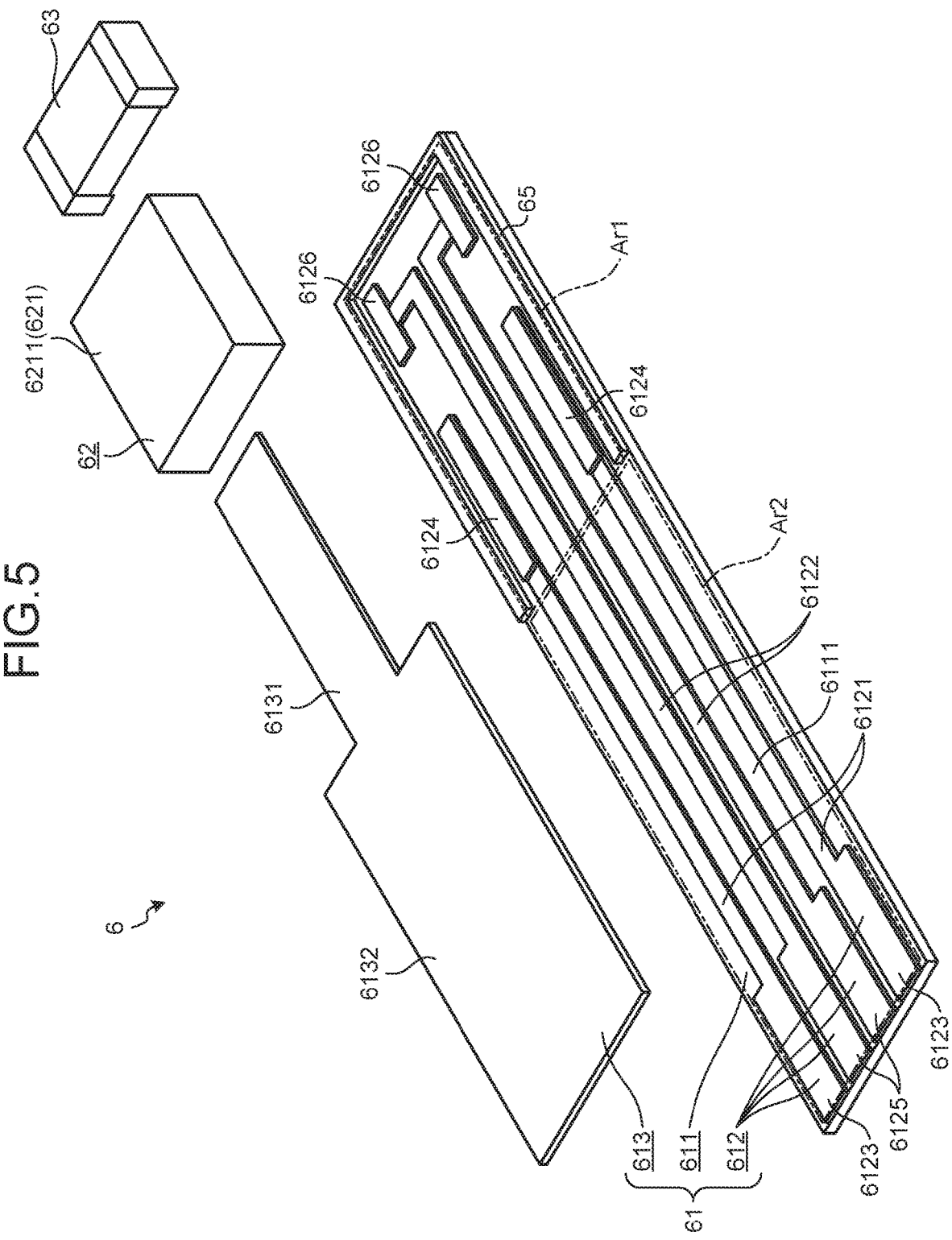
FIG. 5 is an exploded perspective view of the antifogging device illustrated in FIG. 4.

FIG. 3 is a perspective view illustrating the antifogging device 6. FIG. 4 is a diagram obtained by omitting a sealing member 64 from what illustrated in FIG. 3. FIG. 5 is an exploded perspective view of the antifogging device 6 illustrated in FIG. 4.

The antifogging device 6 prevents fogging occurring on the objective lens 2123 under the control of the control device 4. As illustrated in FIGS. 2 to 5, the antifogging device 6 includes a flexible substrate 61, a heater chip (heater) 62, a temperature sensor 63 (FIGS. 2, 4 and 5) and the sealing member 64 (FIG. 3).

For convenience of illustration, FIG. 2 simply illustrates the flexible substrate 61 and does not illustrate the sealing member 64.

The flexible substrate 61 corresponds to the circuit board according to the disclosure. The heater chip 62 and the temperature sensor 63 are mounted on the flexible substrate 61. As illustrated in FIGS. 3 to 5, the flexible substrate 61 includes a base substrate 611, an interconnect unit 612 and a cover member 613.

The base substrate 611 is an insulative and elongated substrate made of, for example, polyimide. One of the substrate surfaces of the base substrate 611 serves as a mount surface 6111 (FIG. 5) on which the heater chip 62 and the temperature sensor 63 are arranged (mounted). The mount surface 6111 corresponds to the "the surface of the circuit board" according to the disclosure.

The interconnect unit 612 is an interconnect pattern that is made of a conductive material, such as a copper foil, and that is formed on the mount surface 6111. As illustrated in FIG. 5, the interconnect unit 612 includes a pair of heater-side interconnects 6121 and a pair of sensor-side interconnects 6122.

As illustrated in FIG. 5, the heater-side interconnects 6121 in a pair are formed to extend along the longitudinal direction of the mount surface 6111 from one end of the mount surface 6111 (left end side in FIG. 5) toward the other end side (right end side in FIG. 5) approximately in parallel. Solder is applied to each of the ends of the heater-side interconnects 6121 in a pair on one side (left ends in FIG. 5) and lead pads 6123 to which the above-described control cable is connected are provided respectively at the ends of the heater-side interconnects 6121. Solder is applied to each of the ends of the heater-side interconnects 6121 in a pair on the other side (right ends in FIG. 5) and heater pads 6124 to which the heater chip 62 is joined are provided respectively at the ends of the heater-side interconnects 6121.

As illustrated in FIG. 5, the sensor-side interconnects 6122 in a pair are positioned between the heater-side interconnects 6121 in a pair and, as the heater-side interconnects 6121 in a pair are, the sensor-side interconnects 6122 in a pair are formed to extend approximately in parallel from one end of the mount surface 6111 toward the other end. Solder is applied to each of the ends of the sensor-side interconnects 6122 in a pair on one side (left ends in FIG. 5) and lead pads 6125 to which the above-described control cable is joined are respectively provided at the ends of the sensor-side interconnects 6122. Solder is applied to each of the ends of the sensor-side interconnects 6122 in a pair on the other side (right ends in FIG. 5) and sensor pads 6126 to which the temperature sensor 63 is joined are respectively provided at the ends of the sensor-side interconnects 6122.

In the first embodiment, as illustrated in FIG. 5, the pair of the sensor-side interconnects 6122 are set longer than the pair of the heater-side interconnects 6121. For this reason, the pair of the sensor pads 6126 positions closer to the other end side (right end side in FIG. 5) of the mount surface 6111 than the pair of the heater pads 6124 is.

As illustrated in FIG. 5, in addition to the above-described interconnects 612, a joining part 65 contacting the sealing member 64 when the sealing member 64 is applied is provided on the mount surface 6111 in order to improve the strength of joining between the flexible substrate 61 (the base substrate 611) and the sealing member 64.

The joining part 65 is made of a metal material, such as a copper foil, as the interconnects 612 are. When the mount surface 6111 is sectioned into two areas that are a first area Ar1 (FIG. 5) on which the heater chip 62 and the temperature sensor 63 are mounted and a second area Ar2 (FIG. 5) excluding the first area Ar1, the joining part 65 is provided in only the first area Ar1.

Specifically, the joining part 65 has a shape of U extending along the periphery of the first area Ar1 in the state where the joining part 65 is exposed to a side surface of the flexible substrate 61.

The cover member 613 includes an insulative substrate that is made of, for example, polyimide as the base substrate 611 is. The cover member 613 is attached onto the mount surface 6111 to cover part of the interconnect unit 612.

Specifically, as illustrated in FIG. 5, the cover member 613 includes: a first cover part 6131 that is attached to the first area Ar1 excluding the pair of the heater pads 6124, the pair of the sensor pads 6126 and the joining part 65; and a second cover part 6132 that is formed integrally with the first cover part 6131 and that is attached to the second area Ar2 excluding the pair of the lead pads 6123 and the pair of the lead pads 6125. In other words, the cover member 613 covers part of the interconnect unit 612 such that the pair of the lead pads 6123, the pair of the lead pads 6125, the pair of the heater pads 6124, the pair of the sensor pads 6126, and the joining part 65 are exposed to the outside.

Figure 6:
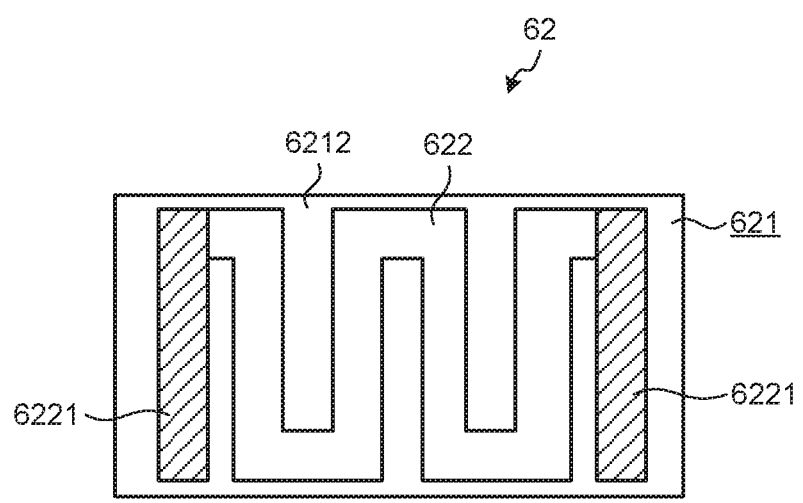
FIG. 6 is a diagram illustrating the back surface of the heater chip illustrated in FIGS. 3 to 5.

FIG. 6 is a diagram illustrating the back surface of the heater chip 62. Specifically, FIG. 6 is a bottom view of the heater chip 62 illustrated in FIGS. 3 to 5.

The heater chip 62 corresponds to the heater according to the disclosure. In the state where the antifogging device 6 is set on the side surface of the frame member 211, the heater chip 62 contacts the side surface of the frame member 211 and applies heat to the objective lens 2123 via the frame member 211, etc. As illustrated in FIG. 6, the heater chip 62 includes a substrate 621 and a metal resistor 622.

The substrate 621 is made of, for example, an insulative substrate made of, for example, ceramics. A surface 6211 (the top surface illustrated in FIGS. 3 to 5) of the substrate 621 functions as a contact surface contacting the side surface of the frame member 211 in the state where the antifogging device 6 is set on the side surface of the frame member 211.

As illustrated in FIG. 6, the metal resistor 622 is formed in a form of a thin film or a paste on a back surface 6212 of the substrate 621 (the bottom surface illustrated in FIGS. 3 to 5) and functions as a heater. Solder is applied to both ends of the metal resistor 622 and pads 6221 in a pair that join to the heater pads 6124 in a pair, respectively, are provided on both ends of the metal resistor 622.

In other words, in the state where the heater chip 62 is mounted on the flexible substrate 61 (the pads 6124 and the pad 6221 are joined), a voltage is applied to the pair of the heater pads 6124 (the pads 6221 in a pair) via the above-described control cable under the control of the control device 4 and accordingly the metal resistor 622 generates heat. The heat of the metal resistor 622 is transmitted to the frame member 211 (the objective lens 2123) via the substrate 621.

Figure 7:
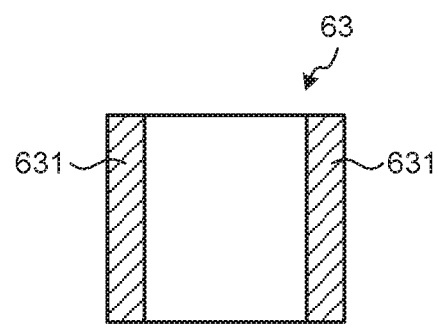
FIG. 7 is a diagram illustrating the back surface of the temperature sensor illustrated in FIGS. 4 and 5.

FIG. 7 is a diagram illustrating the back surface of the temperature sensor 63. Specifically, FIG. 7 is a bottom view of the temperature sensor 63 illustrated in FIGS. 3 to 5.

In the state where the antifogging device 6 is set on the side surface of the frame member 211, the temperature sensor 63 detects the temperature of the side surface of the frame member 211 (the temperature of the distal end area of the endoscope 2 (the insertion unit 21) including the objective lens 2123).

In the embodiment, the temperature sensor 63 is made of a bulk body made of a thermistor material whose resistance varies according to the temperature. As illustrated in FIG. 7, solder is applied to the back surface of the temperature sensor 63 and pads 631 in a pair that are connected respectively to the sensor pads 6126 in a pair are provided.

In other words, in the state where the temperature sensor 63 is mounted on the flexible substrate 61 (the pads 6126 and the pads 631 are joined), the control device 4 reads the resistance of the temperature sensor 63 via the flexible substrate 61 and the above-described control cable, which enables acquisition of temperature information. While recognizing the temperature that is detected by the temperature sensor 63, the control device 4 executes feedback control on the heater chip 62 such that the side surface of the frame member 211 (the objective lens 2123) is maintained at an objective temperature (for example, approximately 39° C.±2° C.).

In the state where the heater chip 62 and the temperature sensor 63 are mounted on the flexible substrate 61, the height from the mount surface 6111 to the surface of the temperature sensor 63 is set smaller than the height from the mount surface 6111 to the surface 6211 of the heater chip 62.

The sealing member 64 is made of a resin material. The sealing member 64 is applied to the mount surface 6111 (only the first area Ar1) and seals the heater chip 62 and the temperature sensor 63.

For the sealing member 64, an epoxy resin material is preferably used because insulative properties, heat resistance and rigidity and long-term reliability as a structure are required. Furthermore, an epoxy resin material containing a silicone component is preferably used for the sealing member 64 in order to prevent a structural failure due to thermal expansion.

Method of Manufacturing Antifogging Device

A method of manufacturing the above-described antifogging device 6 will be described.

The method of manufacturing the antifogging device 6 according to the first embodiment is a method of collectively manufacturing the antifogging devices 6. Prior to descriptions of the method of manufacturing the antifogging device 6, a flexible substrate 61' that is prepared before the manufacturing method will be described.

FIG. 8 is a perspective view illustrating the flexible substrate 61' that is prepared before the method of manufacturing the antifogging device is performed.

As illustrated in FIG. 8, the flexible substrate 61' includes a base substrate 611', interconnect units 612 and a cover member 613'.

The base substrate 611' is made of the same material as that of the above-described base substrate 611 and has a size larger than that of the base substrate 611.

The interconnect units 612 are arranged in parallel in the left-right direction in FIG. 8 on the top surface (the surface corresponding to the mount surface 6111) of the base substrate 611' at given intervals.

As illustrated in FIG. 8, joining parts 65' are arranged in parallel in the right-left direction in FIG. 8 on the top surface of the base substrate 611' as the interconnect units 612 are.

The joining parts 65' are made of the same material as that of the above-described joining part 65 and have the same shape (U-shape) as that of the joining part 65. The joining parts 65' are formed on the top surface of the base substrate 611' such that the joining parts 65' have the same positional relationship with the respective interconnect units 612 as the positional relationship between the joining part 65 and the interconnect unit 612. The joining part 65' has a width larger than that of the above-described joining part 65.

The cover member 613' is made of the same material as that of the above-described cover member 613 and has the same size as that of the base substrate 611'. The cover member 613' is attached to the top surface of the base substrate 611'. As illustrated in FIG. 8, in the cover member 613', first openings 6131' for exposing the respective pairs of the lead pads 6123 and the respective pairs of and the lead pads 6125 of the respective interconnect units 612 to the outside and second openings 6132' for exposing the respective pairs of the heater pads 6124 and the respective pairs of the sensor pads 6126 in the respective interconnect units 612 and the joining parts 65' to the outside are formed.

As described above, the flexible substrate 61' has a size larger than that of the above-described flexible substrate 61. In the flexible substrate 61', each of the rectangular frames Fr represented by chain lines has the same size as that of the above-described flexible substrate 61 (the sum of the first area Ar1 and the second area Ar2). In the flexible substrate 61', the outside of each of the rectangular frames Fr corresponds to the third area according to the disclosure. In other words, each of the rectangular frames Fr corresponds to the "boundary between two areas that are the first area and the second area and the third area" according to the disclosure. The joining parts 65' are formed on the rectangular frames Fr, respectively.

FIG. 9 is a flowchart illustrating the method of manufacturing the antifogging device 6. FIG. 10A to FIG. 10D are diagrams illustrating the method of manufacturing the antifogging device 6.

Figure 10A:
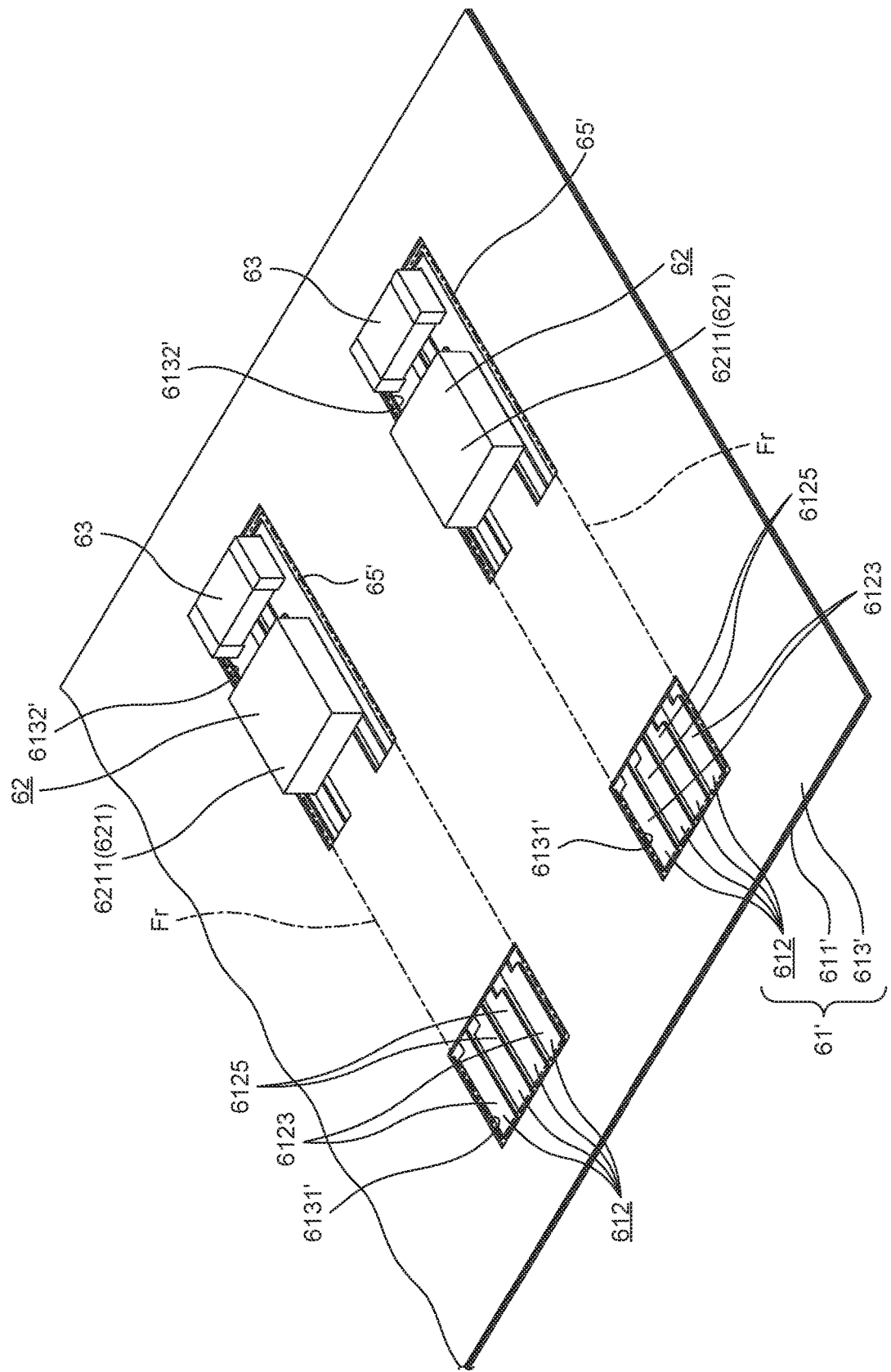
FIG. 10A is a diagram illustrating the method of manufacturing the antifogging device illustrated in FIG. 9.

First of all, as illustrated in FIG. 10A, an operator mounts the heater chips 62 and the temperature sensors 63 on the flexible substrate 61' (step S1: arranging step).

Specifically, the operator applies solder to each of the pairs of the heater pads 6124 and each of the pairs of the sensor pads 6126 on the flexible substrate 61' by, for example, screen printing. The operator then sets the heater chips 62 and the temperature sensors 63 on the flexible substrate 61' (the respective pairs of the heater pads 6124 and the respective pairs of the sensor pads 6126) by using, for example, a mounter. The operator then melts the solder by, for example, reflow soldering to join the heater chips 62 to the pairs of the heater pads 6124, respectively, and join the temperature sensors 63 to the pairs of the sensor pads 6126, respectively.

The operator then cleans the flexible substrate 61' on which the heater chips 62 and the temperature sensor 63 are mounted (the flexible substrate 61' in the state illustrated in FIG. 10A) (step S2: cleaning step).

Specifically, the operator cleans off flux components of the solder and organics, such as oil attached during the operation, remaining on the flexible substrate the flexible substrate 61' (including those on the joining parts 65') by using a dedicated rinse agent or by plasma cleaning.

Figure 10B:
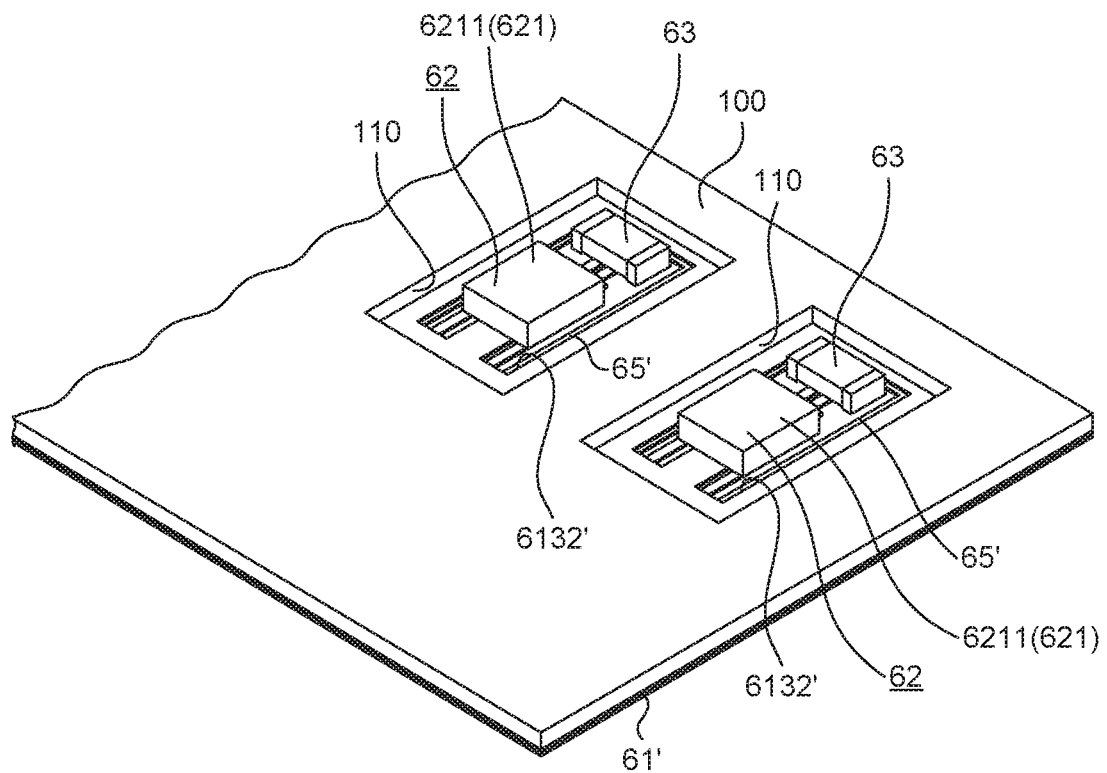
FIG. 10B is a diagram illustrating the method of manufacturing the antifogging device illustrated in FIG. 9.
Figure 10C:
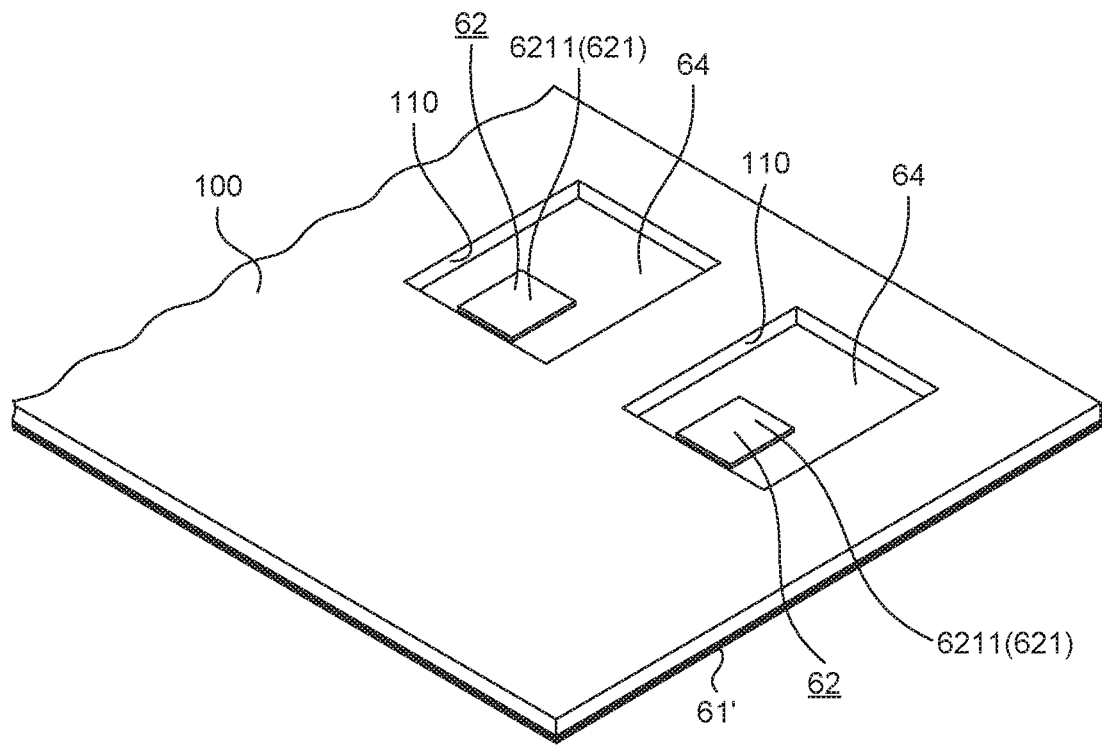
FIG. 10D is a diagram illustrating the method of manufacturing the antifogging device illustrated in FIG. 9.

As illustrated in FIG. 10B, the operator then attaches a thick film member 100 onto the flexible substrate 61' (step S3).

The thick film member 100 is a member serving as a dam when an uncured resin material (the sealing member 64) is injected. The thick film member 100 is formed in the same size as that of the flexible substrate 61' and an adhesive layer (not illustrated) is formed on the back of the thick film member 100. The thick film member 100 is attached onto the flexible substrate 61' with the adhesive layer. The thickness of the thick film member 100 is set equal to or larger than the height from the flexible substrate 61' to the surface 6211 of the heater chip 62. As illustrated in FIG. 10B, in the thick film member 100, injection openings 110 each having a size larger than that of each of second openings 6132' in the cover member 613' are formed in positions corresponding to the second openings 6132'.

As illustrated in FIG. 10O, the operator then injects the uncured resin material (the sealing member 64) into the injection openings 110 and heats the resin to cure the resin (step S4: sealing step).

The operator injects the uncured resin material into the injection openings 110 to a level such that the temperature sensors 63 are buried in the uncured resin material and the surface 6211 of each of the heater chips 62 is exposed to the outside.

If the resin material is highly viscous in the uncured state as the sealing member 64, there is a possibility that, when the uncured resin material is injected into the injection openings 110, the spaces around the heater chips 62 and the temperature sensors 63 are not sufficiently filled with the uncured resin material and thus a filling failure or voids occur. On the other hand, if the resin material is less viscous in the state of being uncured as the sealing member 64, there is a possibility that the uncured resin material permeates into the boundary where the thick film member 100 and the flexible substrate 61' are joined and thus the space is not sufficiently filled with a required amount of the sealing resin. For this reason, in order for the resin material to keep proper fluidity as the sealing member 64 in the state of being uncured, it is preferable that the viscosity before curing be between 5 (Pa·s) to 50 (Pa·s) at 25° C.

Figure 10D:
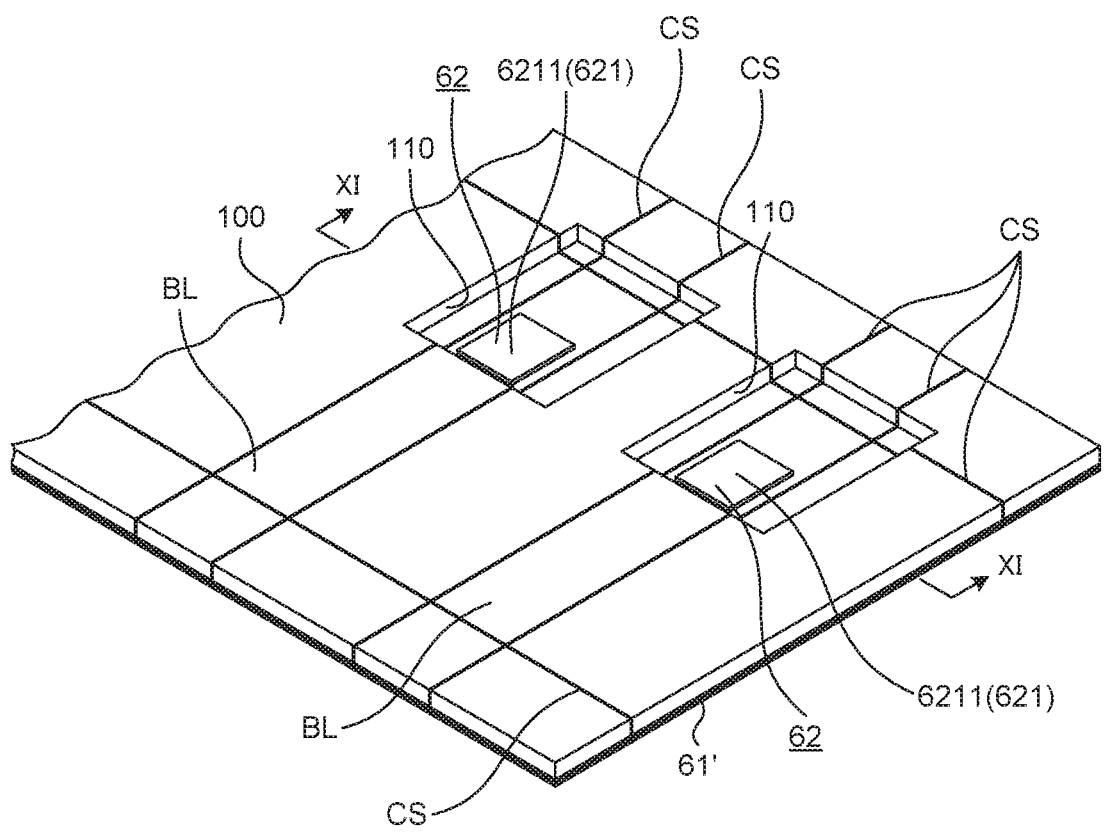

As illustrated in FIG. 10D, for example, the operator cuts the flexible substrate 61', the thick film member 100 and the sealing member 64 by dicing with, for example, a dicer along cutting planes CS (step S5: cutting step).

Figure 11:
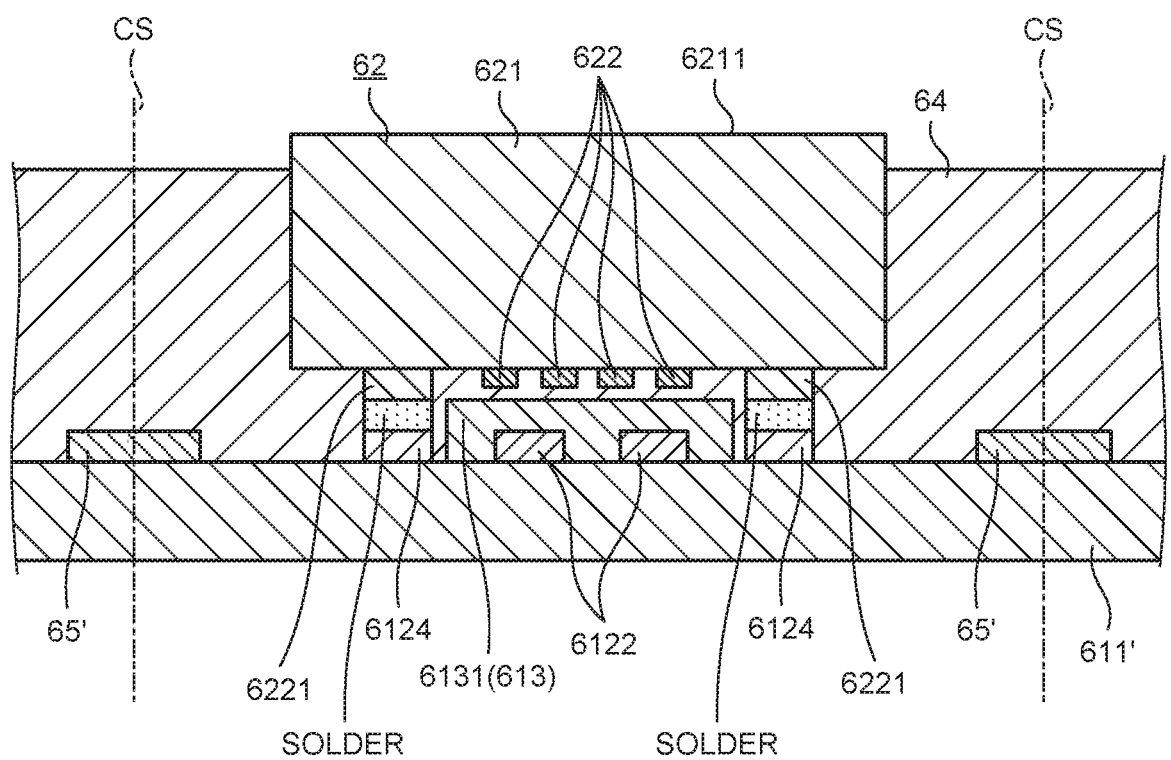
FIG. 11 is a cross-sectional view of what described in FIG. 10D taken along the line XI-XI.

FIG. 11 is a cross-sectional view of what described in FIG. 10D taken along the line XI-XI.

The line XI-XI in FIG. 10D is a line passing through the heater chips 62. FIG. 11 illustrates the cutting planes CS by chain lines.

The cutting planes CS are planes passing along the peripheries of the rectangular frames Fr illustrated in FIG. 10A and extending in the thickness direction of the flexible substrate 61'. In other words, when the flexible substrate 61', the thick film member 100 and the sealing member 64 are cut along the cutting planes CS, each of the joining parts 65' is cut approximately at the center in the width direction as illustrated in FIG. 11.

The operator peels the thick film member 100 from each of blocks BL (FIG. 10D) corresponding to the rectangular frames Fr obtained by the cutting at step S5 (step S6: peeling step).

The antifogging devices 6 (corresponding to what obtained by peeling the thick film member 100 from the blocks BL) are manufactured through the above-described steps.

The cutting step of step S5 and the peeling step of step S6 may be performed inversely. Performing the cutting step first leads to an effect that the flexible substrate 61' is protected from the shocks and contamination during the cutting processing with the thick film member 100. On the other hand, performing the peeling step first leads to an effect that the processing costs are significantly reduced because it suffices if the operation of peeling the thick film member 100 is performed once.

In the antifogging device 6 according to the first embodiment described above, the sealing member 64 is applied to only the first area Ar1 of the mount surface 6111. In other words, the sealing member 64 is applied to only the minimum area for insulative sealing on the heater chips 62 and the temperature sensors 63. Accordingly, it is possible to perform insulative sealing without fail on the heater chip 62 and the temperature sensor 63, reduce the size of the antifogging device 6, and thus reduce the size of the endoscope 2.

In the antifogging device 6 according to the first embodiment, the joining part 65 is provided on the flexible substrate 61 (the base substrate 611) and the joining part 65 contacts the sealing member 64. The joining part 65 is made of a metal material having a relatively high strength of joining with the resin material. For this reason, compared with the configuration without the joining part 65, it is possible to prevent the sealing member 64 from peeling from the flexible substrate 61.

When the joining part 65 is provided at a position apart from the side surface (periphery) of the flexible substrate 61 on the mount surface 6111, the following problem may occur.

Specifically, as the joining part 65 is not provided on the periphery of the flexible substrate 61, the strength of joining between the flexible substrate 61 and the sealing member 64 on the periphery is low. For this reason, when an external force is applied to the side surface (the periphery) of the antifogging device 6, the sealing member 64 peels from the flexible substrate 61 on the periphery. The momentum of the peeling of the sealing member 64 on the periphery causes the sealing member 64 to peel also from the joining part 65 that is provided at the position apart from the periphery. This leads to a problem in that providing the joining part 65 in a position apart from the side surface (periphery) of the flexible substrate 61 has a risk in that the sealed state of the heater chip 62 and the temperature sensor 63 is lost eventually.

To deal with the problem, in the antifogging device 6 according to the first embodiment, the joining part 65 has a shape of U extending along the periphery in the first area Ar1 in the state where the joining part 65 is exposed to the side surface of the flexible substrate 61. This makes it is possible to improve the strength of joining between the flexible substrate 61 (the joining part 65) and the sealing member 64 on the periphery serving as a point at which the sealing member 64 starts peeling from the flexible substrate 61. Accordingly, it is possible to preferably maintain the state where the heater chip 62 and the temperature sensor 63 are sealed without causing the above-described peeling of the sealing member 64.

Accordingly, the antifogging device 6 according to the first embodiment realizes an effect that it is possible to improve the durability while enabling size reduction.

The method of manufacturing the antifogging device 6 according to the first embodiment includes the arranging step (step S1), the sealing step (step S4) and the cutting step (step S5), thereby enabling collective manufacturing of the antifogging devices 6.

Particularly, in the flexible substrate 61' used in the manufacturing method, the joining parts 65' are provided on the cutting planes CS along which the cutting is performed at the cutting step (step S5). Thus, even when an external force is applied to the cutting planes CS (corresponding to the periphery of the flexible substrate 61) with, for example, a dicer at the cutting step (step S5), the strength of joining between the flexible substrate 61 and the sealing member 64 near the cutting planes CS is improved by the joining parts 65' and therefore it is possible to prevent the sealing member 64 from peeling from the flexible substrate 61' (the joining parts 65').

Furthermore, the method of manufacturing the antifogging device 6 according to the first embodiment includes the cleaning step (step S2) between the arranging step (step S1) and the sealing step (step S4). Accordingly, it is possible to remove the flux components of the solder and organics, such as oil attached during the operation, remaining on the joining parts 65' before the sealing step (step S4). It is thus possible to further make the strength of joining between the joining parts 65' and the sealing member 64 further rigid and to achieve the above-described effect (of enabling prevention of the sealing member 64 from peeling from the flexible substrate 61' (the joining part 65')) more preferably.

Second Embodiment

A second embodiment of the disclosure will be described.

In the following descriptions, the same components as those of the first embodiment are denoted with the same reference numbers as those of the first embodiment and detailed descriptions thereof will be omitted or simplified.

In the antifogging device 6 according to the above-described first embodiment, the joining part 65 is formed on the flat mount surface 6111.

On the other hand, in an antifogging device according to the second embodiment, a setting area having a thickness smaller than those of other areas is provided in a position where a joining part is formed on the periphery of a mount surface. The joining part is formed in the setting area.

A configuration of an antifogging device 6A according to the second embodiment will be described below.

Configuration of Antifogging Device

Figure 12:
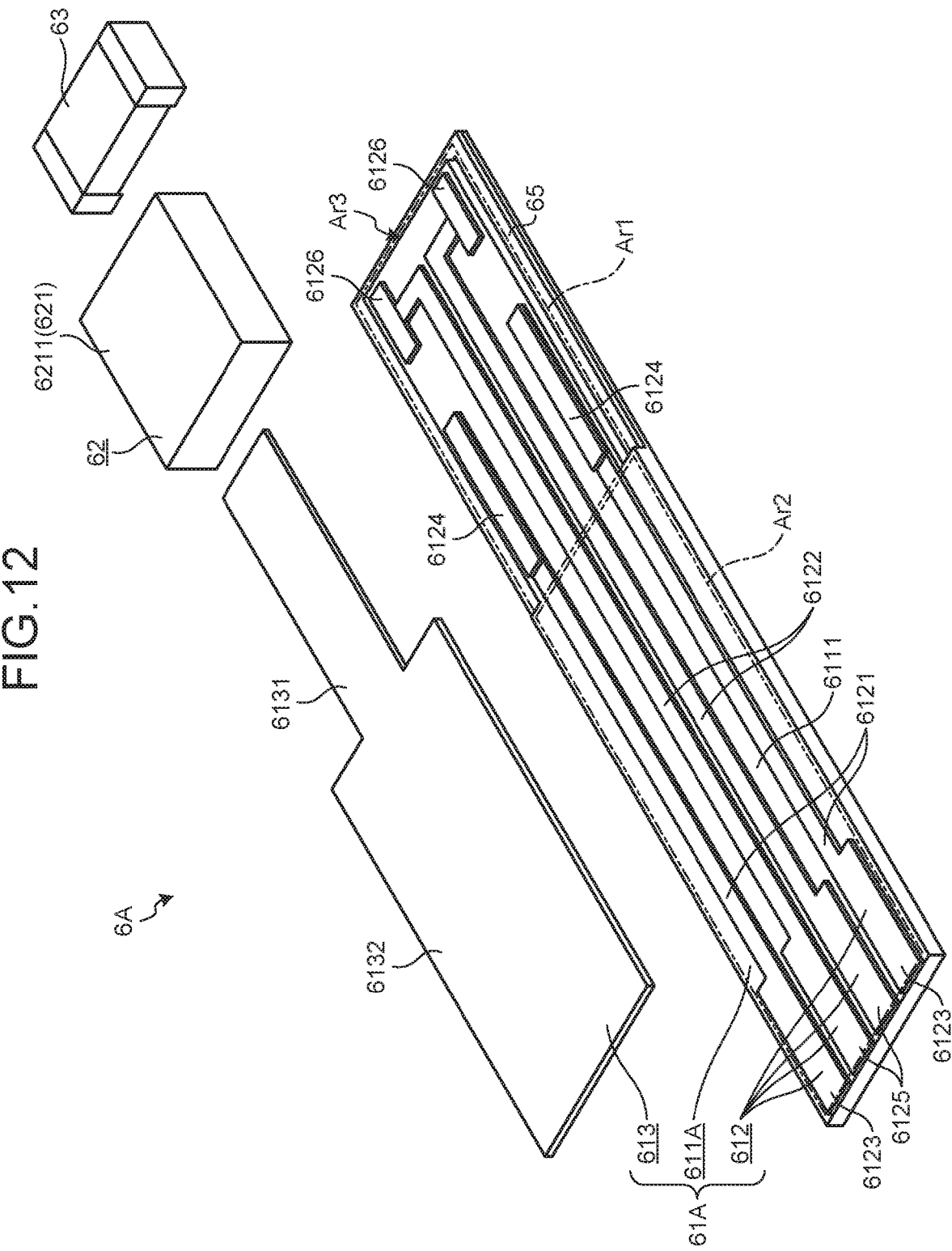
FIG. 12 is a diagram illustrating an antifogging device according to a second embodiment of the disclosure.

FIG. 12 is a diagram illustrating the antifogging device 6A according to the second embodiment of the disclosure. Specifically, FIG. 12 is an exploded perspective view corresponding to FIG. 5, where the sealing member 64 is omitted.

As illustrated in FIG. 12, the antifogging device 6A according to the second embodiment is different from the antifogging device 6 according to the above-described first embodiment (FIGS. 3 to 5) in that a base substrate 611A (a flexible substrate 61A) having a shape different from that of the base substrate 611 is used.

In the base substrate 611A, a setting area Ar3 having a thickness smaller than those of other areas is provided in the peripheral area (U-shaped) of the first area Ar1 as illustrated in FIG. 12. The joining part 65 according to the second embodiment is formed on the setting area Ar3.

The thickness of the joining part 65 is set smaller than the height of the step between the setting area Ar3 and other areas.

The configuration of the flexible substrate 61A excluding the base substrate 611A is the same as that of the flexible substrate 61 according to the above-described first embodiment.

Method of Manufacturing Antifogging Device

The method of manufacturing the antifogging device 6A according to the second embodiment will be described.

The method of manufacturing the antifogging device 6A according to the second embodiment is the same as the method of manufacturing the antifogging device 6 (FIG. 9) according to the above-described first embodiment; however, a flexible substrate 61A' (a base substrate 611A') different from the flexible substrate 61' (the base substrate 611') according to the above-described first embodiment is used as a flexible substrate (base substrata) that is prepared in advance before the manufacturing method.

Figure 13:
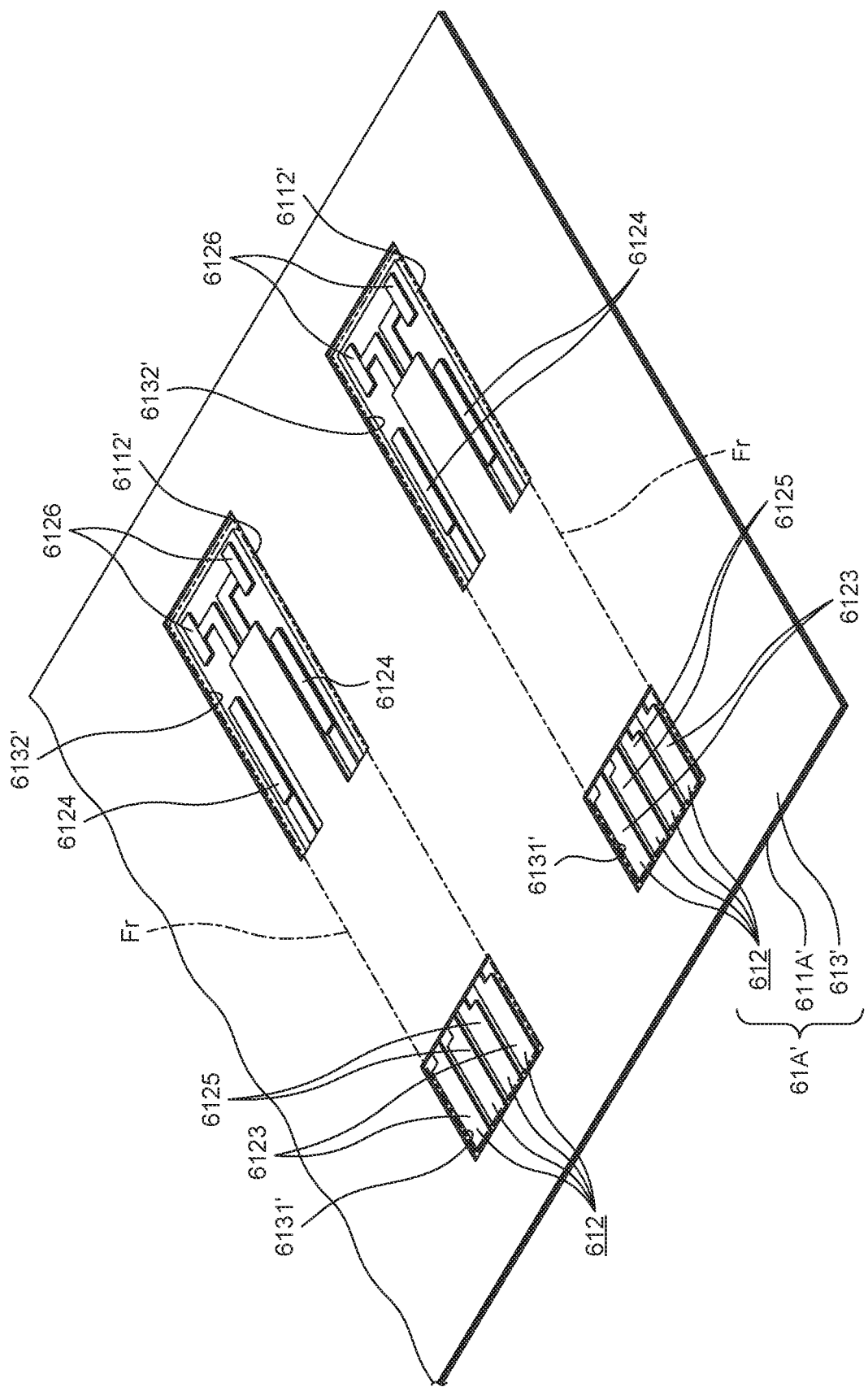
FIG. 13 is a perspective view illustrating a flexible substrate that is prepared before a method of manufacturing the antifogging device illustrated in FIG. 12 is performed.

FIG. 13 is a perspective view illustrating the flexible substrate 61A' that is prepared before the method of manufacturing the antifogging device according to the second embodiment is performed.

In the base substrate 611A', grooves 6112' corresponding to the above-described setting areas Ar3 are formed respectively in U-shaped parts each surrounding a pair of the heater pads 6124 and a pair of the sensor pads 6126 in each of the rectangular frames Fr. The joining parts 65' are formed respectively on the bottom parts of the grooves 6112' (see FIG. 14).

The flexible substrate 61A' excluding the base substrate 611A' has the same configuration as that of the flexible substrate 61' (FIG. 8) according to the above-described first embodiment.

Figure 14:
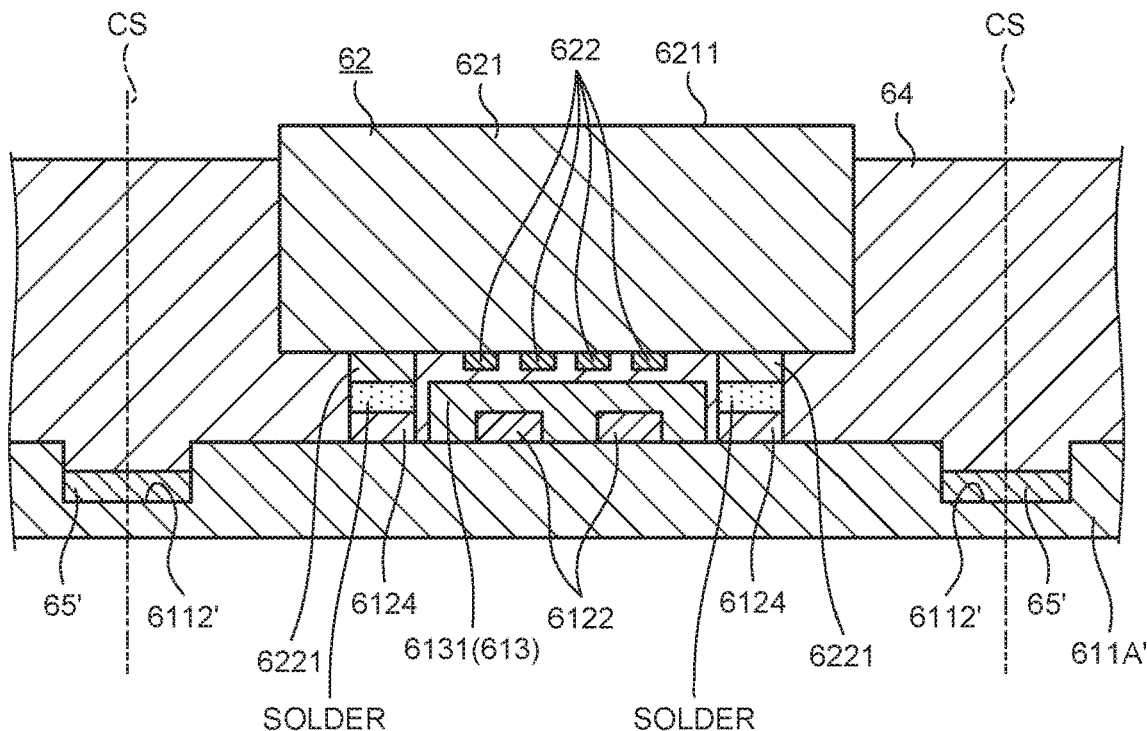
FIG. 14 is a diagram illustrating the method of manufacturing the antifogging device according to the second embodiment (step S5)

FIG. 14 is a diagram illustrating the method of manufacturing the antifogging device according to the second embodiment (step S5). Specifically, FIG. 14 is a cross-sectional view corresponding to FIG. 11.

The cutting planes CS along which the cutting is performed at step S5 are planes passing along the peripheries of the rectangular frames Fr illustrated in FIG. 13 and extending in the thickness direction of the flexible substrate 61A'. In other words, the cutting planes CS pass through the grooves 6112'. For this reason, when the flexible substrate 61A', the thick film member 100 and the sealing member 64 are cut along the cutting planes CS, the joining parts 65' are cut approximately at the center in the width direction as illustrated in FIG. 14.

The antifogging device 6A according to the second embodiment achieves the following effect in addition to the same effect as that of the above-described first embodiment.

In the antifogging device 6A according to the second embodiment, the setting area Ar3 having a thickness smaller than those of other areas is provided in the periphery area (U-shaped) of the first area Ar1 in the base substrate 611A. The joining part 65 is formed on the setting area Ar3. In other words, providing the setting areas Ar3 increases the area of contact between the flexible substrate 61A (the base substrate 611A) and the sealing member 64.

Thus, the increase of the area of contact in addition to improvement of the strength of joining between the flexible substrate 61A and the sealing member 64 makes it possible to improve the strength of joining between the flexible substrate 61A (the base substrate 611A) and the sealing member 64. It is thus possible to preferably realize the effect of the above-described first embodiment (the effect of enabling size reduction and improvement of the durability).

Particularly, the walls of the setting areas Ar3 (the groove 6112') have fine irregularities due to formation of the grooves 6112' in the base substrate 611A'. The sealing member 64 getting into the fine irregularities (anchor effect) further increases the strength of joining between the sealing member 64 and the base substrate 611A.

Modification of Second Embodiment

In the above-described second embodiment, a configuration in which the joining part 65 is provided also on the side wall in the setting area Ar3 (a configuration in which the joining part 65' is provided also on the side wall of the groove 6112') may be employed. When such a configuration is employed, the joining part 65 (the joining part 65') is L-shaped in a cross section.

Third Embodiment

A third embodiment of the disclosure will be described.

In the following descriptions, the same components as those of the first embodiment are denoted with the same reference numbers and detailed descriptions thereof will be omitted or simplified.

The method of manufacturing the antifogging device 6 according to the third embodiment is different from the method according to the first embodiment.

The method of manufacturing the antifogging device 6 according to the third embodiment will be described below.

Method of Manufacturing Antifogging Device

Figure 15:
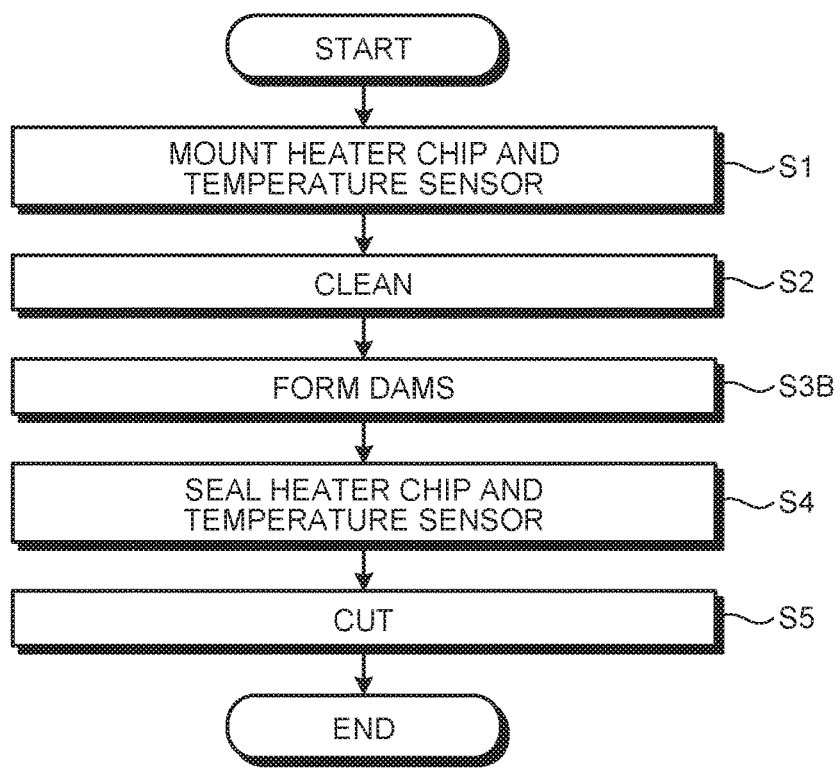
FIG. 15 is a flowchart illustrating a method of manufacturing an antifogging device according to a third embodiment of the disclosure.
Figure 16:
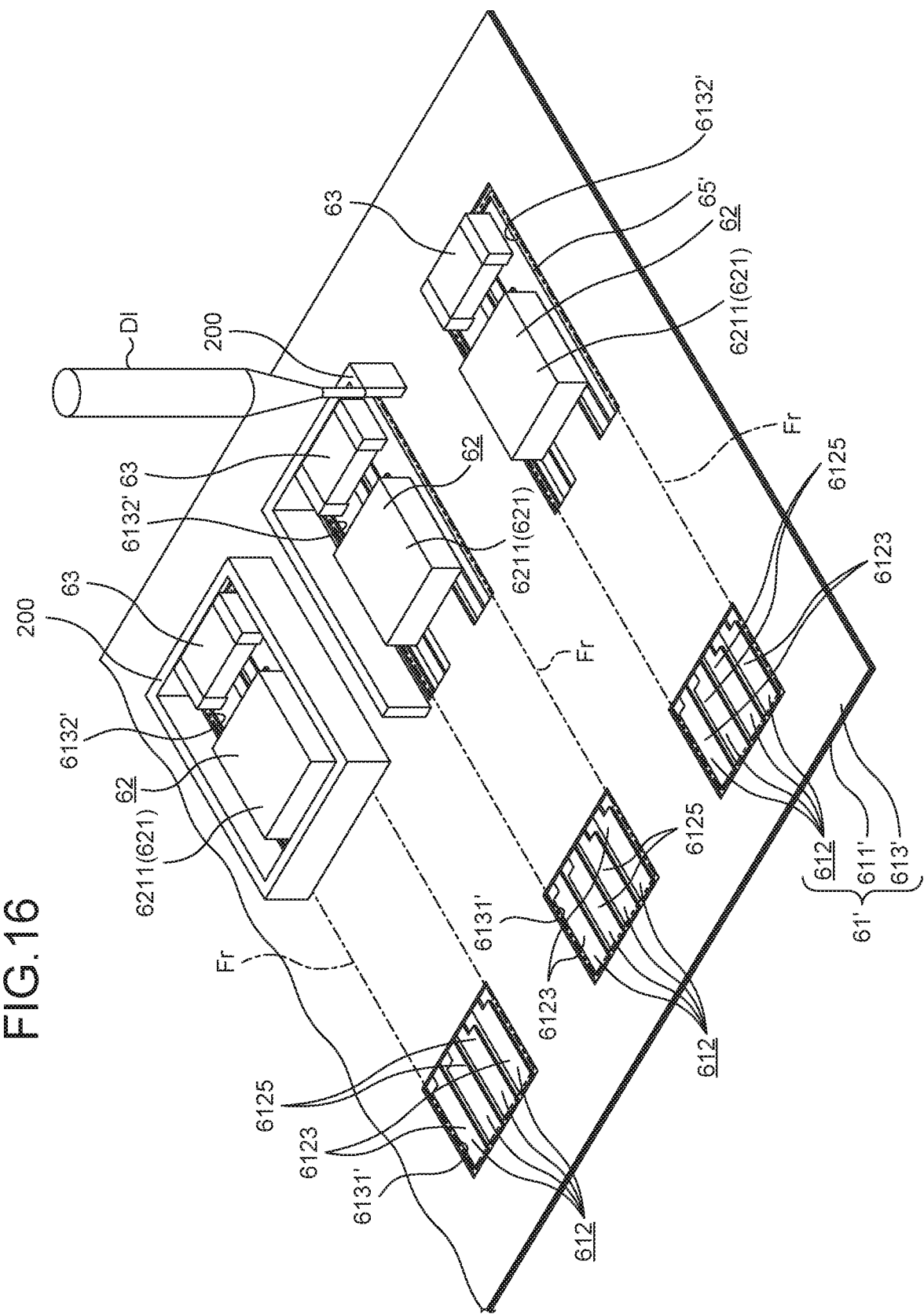
FIG. 16 is a diagram illustrating the method of manufacturing an antifogging device illustrated in FIG. 15.

FIG. 15 is a flowchart illustrating the method of manufacturing the antifogging device 6 according to the third embodiment. FIG. 16 is a diagram illustrating the method of manufacturing the antifogging device 6.

As illustrated in FIG. 15, the method of manufacturing the antifogging device 6 according to the third embodiment is different from the method of manufacturing the antifogging device 6 according to the first embodiment (FIG. 9) in that step S6 is omitted and step S3B is employed instead of step S3.

For this reason, only step S3B will be described below.

As illustrated in FIG. 16, the operator forms dams 200 on the flexible substrate 61' by using, for example, a dispenser DI (step S3B).

As the thick film member 100 (FIG. 10B) according to the above-described first embodiment are, the dams 200 are members serving as dams when an uncured resin material (the sealing member 64) is injected. In other words, as illustrated in FIG. 16, the dams 200 are respectively provided in positions corresponding to the second openings 6132' in the cover member 613' and each of the dams 200 has a shape of a frame having a size larger than the second opening 6132' (the same size as that of the opening face of the injection opening 110 according to the above-described first embodiment). The height of the dams 200 (the height from the flexible substrate 61') is set equal to the thickness of the thick film member 100 according to the above-described first embodiment.

The operator then injects the uncured resin material (the sealing member 64) for sealing into the dams 200 and cures the uncured resin material after step S3B (step S4) and performs the same cutting step (step S5) as that of the first embodiment.

The method of manufacturing the antifogging device 6 according to the third embodiment described above realizes the following effect in addition to the effect of the above-described first embodiment.

If the thick film member according to the first embodiment is used for the method of manufacturing the antifogging device, there is a possibility that a difference in thermal expansion between the thick film member and the flexible substrate when the sealing member is cured causes an occurrence of warpage of the flexible substrate. The method of manufacturing the antifogging device according to the third embodiment can prevent such an occurrence of warpage of the flexible substrate.

If the thick film member according to the first embodiment is used for the method of manufacturing the antifogging device, there is a possibility that the sealing member leaks from the boundary where the thick film member and the flexible substrate are joined unless the thick film member is securely attached onto the flexible substrate. The method of manufacturing the antifogging device according to the third embodiment can prevent such an occurrence of leakage of the sealing member.

Other Embodiments

The embodiments for carrying out the disclosure have been described; however, the disclosure should not be limited to only the above-described first to third embodiments.

In the first to third embodiments, the antifogging device 6 or 6A according to the disclosure is mounted on the endoscope 2 (rigid endoscope) using a rigid scope (the insertion unit 21). Alternatively, the antifogging device 6 or 6A may be mounted on a soft endoscope using a soft endoscope (not illustrated) may be mounted on the endoscope 2. Furthermore, the antifogging device 6 or 6A according to the disclosure may be mounted on an industrial endoscope other than medical endoscopes. Furthermore, the antifogging device 6 or 6A according to the disclosure may be mounted on another device (such as an imaging device, such as a camera), other than endoscopes, including an optical member having a risk of occurrence of fogging.

In the first to third embodiments, the joining part 65 is made of a metal material, such as a copper foil. Alternatively, the joining part 65 may be made of a metal material other than copper as long as the material is an inorganic material or may be made of a material, such as glass.

In the first to third embodiments, irregularities may be provided by, for example, blasting on a contact surface of at least any one of the heater chip 62, the temperature sensor 63 and the flexible substrate 61 or 61A, the contact surface being a surface of contact with the sealing member 64.

When such a configuration is employed, the sealing member 64 enters the irregularities (because of anchor effect) and thus it is possible to further increase the strength of joining between the sealing member 64 and the flexible substrate 61 or 61A.

In the first to third embodiments, the temperature sensor 63 is arranged closer to the other end (on the right end side in FIG. 5) of the mount surface 6111 on the mount surface 6111 than the heater chip 62 is. Alternatively, the positional relationship between the temperature sensor 63 and the heater chip 62 may be set inverse to the positional relationship according to the above-described first to third embodiments.

In the first to third embodiments, the temperature sensor 63 is made of a thermistor. Alternatively, the configuration where a ceramic insulative substrate serves as a substrate may be used as in the case of the heater chip 62.

The method of manufacturing the antifogging device 6 according to the above-described first to third embodiments (FIGS. 9 and 15) may be applied to the method of manufacturing an antifogging device 6C having the following configuration.

Figure 17:
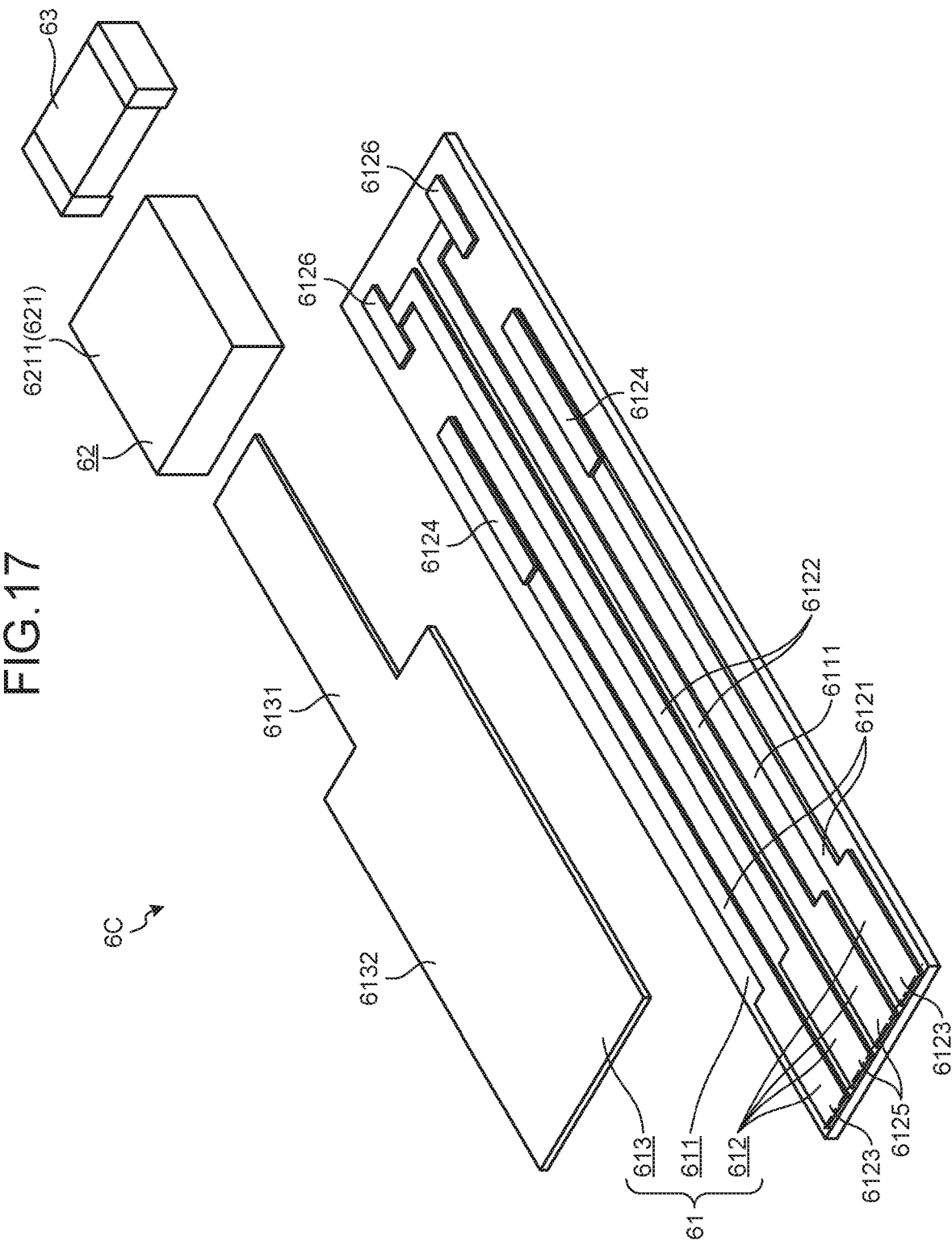
FIG. 17 is a diagram illustrating an antifogging device according to a modification of the first to third embodiments of the disclosure.

FIG. 17 is a diagram illustrating the antifogging device 6C according to a modification of the first to third embodiments of the disclosure. Specifically, FIG. 17 is an exploded perspective view corresponding to FIG. 5 where the sealing member 64 is omitted.

As illustrated in FIG. 17, the antifogging device 6C according to the modification is different from the antifogging device 6 (FIGS. 3 to 5) according to the above-described first embodiment in that the joining part 65 is omitted.

It is possible to manufacture the antifogging device 6C by preparing the flexible substrate obtained by omitting the joining parts 65' from the flexible substrate 61' illustrated in FIG. 8 and performing the same method as the method of manufacturing the antifogging device 6 according to the above-described first to third embodiments (FIG. 9 or 15) by using the flexible substrate.

Figure 18:
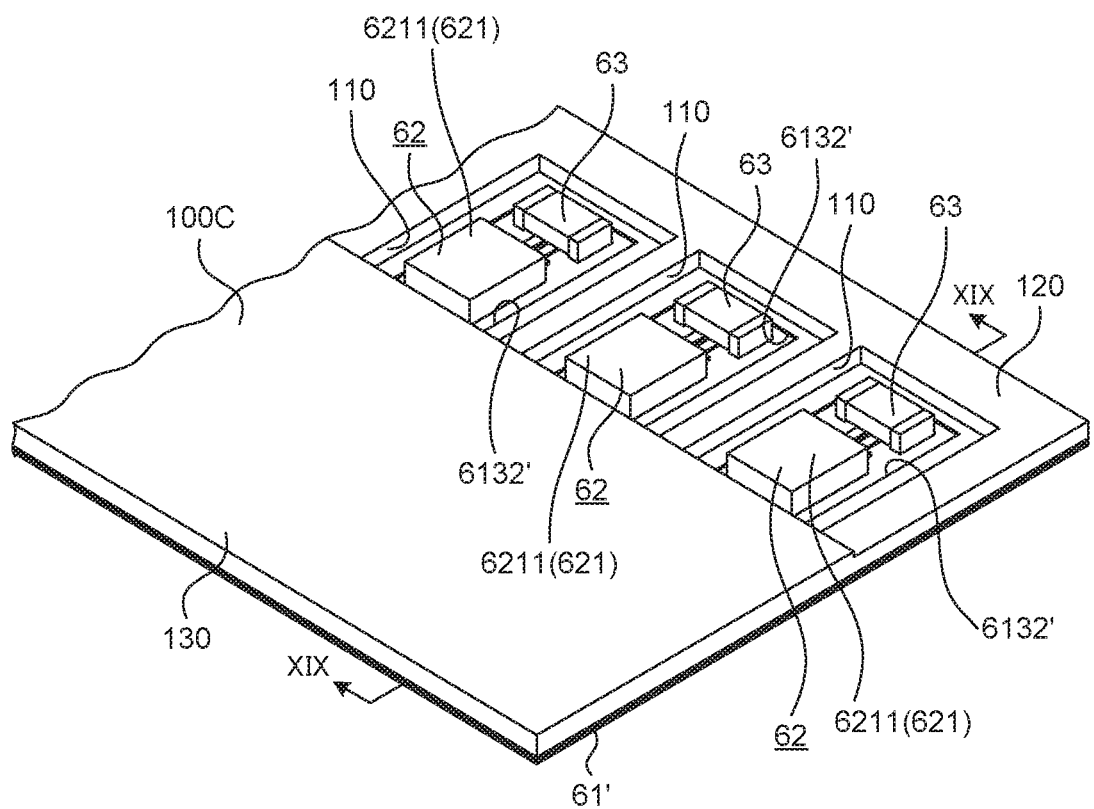
FIG. 18 is a diagram illustrating an exemplary thick film member that is used for a method of manufacturing the antifogging device illustrated in FIG. 17.
Figure 19:
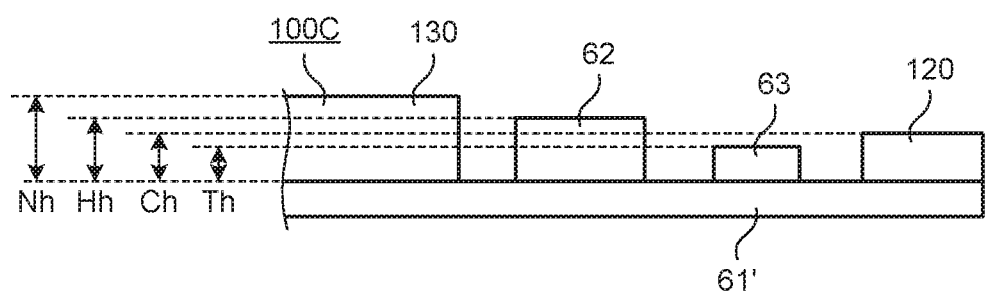
FIG. 19 is a diagram illustrating the exemplary thick film member that is used for the method of manufacturing the antifogging device illustrated in FIG. 17.

FIGS. 18 and 19 are diagrams illustrating an exemplary thick film member 100C used in the method of manufacturing the antifogging device 6C. Specifically, FIG. 18 is a diagram corresponding to FIG. 10B (diagram illustrating the state where step S3 is performed). FIG. 19 is a cross-sectional view of what illustrated in FIG. 18, taken along the line XIX-XIX.

The line XIX-XIX in FIG. 18 is a line passing through the injection opening 110 of the thick film member 100C.

Instead of the thick film member 100 according to the above-described first embodiment, the thick film member 100C illustrated in FIG. 18 may be used as the thick film member used in the above-described method of manufacturing the antifogging device 6C (FIG. 9).

As illustrated in FIG. 18, compared to the thick film member 100 according to the above-described first embodiment, the thickness of a first part 120 on the side of the first area Ar1 and the thickness of a second part 130 on the side of the second area Ar2 are set at different thicknesses at the boundary between the first areas Ar1 and the second areas Ar2.

Specifically, as illustrated in FIG. 19, the thickness of the thick film member 100C is set to satisfy $Nh \geq Hh > Ch > Th$, where Nh is a thickness of the second part, Ch is a thickness of the first part 120, Hh is a height of the heater chip 62 and Th is a height of the temperature sensor 63.

In the case where the thick film member 100C is used, when the uncured resin material (the sealing member 64) is injected into the injection openings 110 at step S4, the excess of the resin material flows out of the injection openings 110 and flows out of the injection openings 110. Accordingly, it is possible to easily set the resin material at a given height (the thickness Ch of the first part 120).

The thick film member 100C may be used in the method of manufacturing the antifogging device 6 or 6A according to the above-described first or second embodiment.

The modifications illustrated in FIGS. 17 to 19 include the following additional items.

Additional Item 1

A method of manufacturing an antifogging device in which a heater and a temperature sensor are arranged on a circuit board that includes, before the manufacturing, a first area where the heater and the temperature sensor are arranged and a third area that is provided outside the first area, the method comprising:

arranging the heater and the temperature sensor on the circuit board;

sealing the heater and the temperature sensor by applying, over the first area and the third area, a sealing member made of a resin material on a surface of the circuit board on which the heater and the temperature sensor are arranged; and cutting the circuit board along a boundary between the first area and the third area.

Additional Item 2

The method according to additional item 1, further comprising forming walls surrounding at least the heater and the temperature sensor on the surface after the arranging and before the sealing, wherein the sealing includes injecting the uncured sealing member in a space surrounded by the walls and curing the sealing member.

Additional Item 3

The method according to additional item 1, further comprising:

adhering a thick film member having an injection opening through which the heater and the temperature sensor are insertable to the surface after the arranging and before the sealing; and peeling the thick film member from the surface after the sealing, wherein the sealing includes injecting the uncured sealing member into the injection opening and curing the sealing member.

Additional Item 4

The method according to additional item 3, wherein, when the thick film member is sectioned into two parts that are the first part having the injection opening and a second part other than the first part at part of the inner periphery of the injection opening serving as a boundary, a setting is made for the thick film member to satisfy a relationship of $Nh \geq Hh > Ch > Th$, where Ch is a thickness of the first part, Nh is a thickness of the second part, Hh is a height of the heater chip from the circuit board, and Th is a height from the circuit board to the temperature sensor.

The "walls" according to additional item 2 corresponds to the dam 200 illustrated in FIG. 16. The "forming" according to additional item 2 corresponds to step S3B illustrated in FIG. 15. The "adhering" and "peeling" according to additional item 3 correspond to step S3 and step S6 illustrated in FIG. 9, respectively.

The method of manufacturing the antifogging device 6, 6A or 6C is not limited to the order of steps in the flowcharts (FIG. 9 and FIG. 15) according to the above-described first to third embodiments and the modifications thereof and the order may be changed as long as no inconsistency is caused.

The antifogging devices, the endoscope devices, and the methods of manufacturing an antifogging device according to the embodiments realize an effect of enabling size reduction and improvement of the durability.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An antifogging device comprising:
   a heater configured to apply heat to an optical member;
   a temperature sensor configured to detect a temperature;
   a circuit board with a first surface on which the heater and the temperature sensor are mounted;
   a sealing member that is made of a resin material and that is applied to the first surface to seal the heater and the temperature sensor; and
   a joining part that is provided on at least a portion of the first surface, the joining part being made of an inorganic material, the joining part being configured to:
     extend along a peripheral edge of the first surface such that the joining part is exposed to a side surface of the circuit board; and
     contact the sealing member,
   wherein the side surface of the circuit board being adjacent to the first surface and offset from the first surface.

2. The antifogging device according to claim 1, wherein when the first surface is sectioned into a first area where the heater and the temperature sensor are arranged and a second area other than the first area, the sealing member is applied to only the first area, and
   the joining part is provided to only the first area and has a U shape surrounding the heater and the temperature sensor when viewed in a thickness direction of the circuit board.

3. The antifogging device according to claim 1, wherein the inorganic material is a metal material.

4. The antifogging device according to claim 2, wherein a setting area having a thickness smaller than those of the first area is set on at least part of the peripheral edge of the first surface, and
   the joining part is provided in the setting area.

5. The antifogging device according to claim 1, wherein irregularities are provided on a contact surface of at least any one of the heater, the temperature sensor and the circuit board, the contact surface being a surface of contact with the sealing member.

6. An endoscope device comprising:
   an optical member; and
   the antifogging device according to claim 1 configured to prevent fogging occurring on the optical member.

* * * * *